United States Patent
Maria De Boer et al.

(10) Patent No.: US 7,589,245 B2
(45) Date of Patent: Sep. 15, 2009

(54) PROCESS FOR PREPARING LINEAR ALPHA OLEFINS

(75) Inventors: Eric Johannes Maria De Boer, Amsterdam (NL); Harry Van Der Heijden, Amsterdam (NL); Inge Oosterveld, Amsterdam (NL); Arie Van Zon, Amsterdam (NL)

(73) Assignee: Shell Oil Company, Houston, TX (US)

( * ) Notice: Subject to any disclaimer, the term of this patent is extended or adjusted under 35 U.S.C. 154(b) by 884 days.

(21) Appl. No.: 11/179,459

(22) Filed: Jul. 12, 2005

(65) Prior Publication Data

US 2006/0014989 A1    Jan. 19, 2006

(30) Foreign Application Priority Data

Jul. 13, 2004    (EP) .................. 04254169

(51) Int. Cl.
C07C 2/26    (2006.01)
C07C 2/34    (2006.01)

(52) U.S. Cl. .................. 585/328; 585/329; 585/510; 585/511

(58) Field of Classification Search ................. 585/328, 585/329, 510, 511
See application file for complete search history.

(56) References Cited

U.S. PATENT DOCUMENTS

| | | | |
|---|---|---|---|
| 4,728,583 A | 3/1988 | Yamazaki et al. | 428/690 |
| 4,869,210 A | 9/1989 | Wittchow | 122/406 |
| 4,912,333 A | 3/1990 | Roberts et al. | 250/487.1 |
| 4,944,026 A | 7/1990 | Arakawa et al. | 250/484.1 |
| 5,124,465 A | 6/1992 | Allen et al. | 556/190 |
| 5,151,604 A | 9/1992 | Kohda et al. | 250/484.1 |
| 5,191,145 A | 3/1993 | Allen et al. | 585/665 |
| 5,318,935 A | 6/1994 | Canich et al. | 502/117 |
| 5,607,774 A | 3/1997 | Dahlquist et al. | 428/447 |
| 5,726,115 A | 3/1998 | Horton et al. | 502/152 |
| 5,830,629 A | 11/1998 | Vizard et al. | 430/523 |
| 5,888,647 A | 3/1999 | Yamane | 428/338 |
| 5,905,014 A | 5/1999 | Van de Bergh | 430/139 |
| 5,955,555 A | 9/1999 | Bennett | 526/161 |
| 6,013,946 A | 1/2000 | Lee et al. | 585/523 |
| 6,063,881 A | 5/2000 | Bennett | 526/161 |
| 6,103,946 A | 8/2000 | Brookhart, III et al. | 585/523 |
| 6,150,482 A | 11/2000 | Brookhart, III et al. | 526/161 |
| 6,214,761 B1 | 4/2001 | Bennett | 502/117 |
| 6,232,259 B1 | 5/2001 | Ittel et al. | 502/155 |
| 6,291,733 B1 | 9/2001 | Small et al. | 585/512 |
| 6,310,153 B2 | 10/2001 | Ittel et al. | 525/172 |
| 6,395,668 B1 | 5/2002 | van Baar et al. | 502/123 |
| 6,407,188 B1 | 6/2002 | Guan et al. | 526/113 |
| 6,414,098 B1 | 7/2002 | Engehausen et al. | 526/161 |
| 6,417,305 B2 | 7/2002 | Bennett | 526/161 |
| 6,417,364 B1 | 7/2002 | Lenges | 546/12 |
| 6,423,848 B2 | 7/2002 | Bennett | 546/329 |
| 6,432,862 B1 | 8/2002 | Bennett | 502/117 |
| 6,441,117 B1 | 8/2002 | Cameron | 526/352 |
| 6,451,939 B1 | 9/2002 | Britovsek et al. | 526/161 |
| 6,455,660 B1 | 9/2002 | Clutton et al. | 526/352 |
| 6,458,672 B1 | 10/2002 | Henley et al. | 438/478 |
| 6,458,739 B1 | 10/2002 | Kimberley et al. | 502/155 |
| 6,458,905 B1 | 10/2002 | Schmidt et al. | 526/172 |
| 6,461,994 B1 | 10/2002 | Gibson et al. | 502/155 |
| 6,462,152 B1 | 10/2002 | Berardi et al. | 526/75 |
| 6,462,155 B1 | 10/2002 | Okuda | 526/161 |
| 6,465,386 B1 | 10/2002 | Maddox et al. | 502/155 |
| 6,472,341 B1 | 10/2002 | Kimberley et al. | 502/155 |
| 6,479,601 B1 | 11/2002 | Kerns et al. | 526/161 |
| 6,489,497 B1 | 12/2002 | Brookhart, III et al. | 556/138 |
| 6,521,329 B2 | 2/2003 | Aylward et al. | 428/212 |

(Continued)

FOREIGN PATENT DOCUMENTS

| | | |
|---|---|---|
| EP | 0 505 834 A1 | 3/1992 |
| EP | 1125928 | 8/2001 |
| EP | 1127987 | 8/2001 |
| SU | 418462 | 9/1974 |
| WO | 2004/037415 A2 | 5/2004 |

OTHER PUBLICATIONS

Britovsek G J P et al: "Iron-Catalyzed Polyethylene Chain Growth on Zinx: Linear Alpha-Olefins with a Poisson Distribution" Angewandte Chemie. International Edition, Wiley-VCH, Weinheim, DE, vol. 41, No. 3, Jan. 29, 2002, pp. 484-491, XP002286464.

(Continued)

*Primary Examiner*—Thuan Dinh Dang

(57) ABSTRACT

A process for the preparation of linear alpha olefins having 2n carbon atoms from linear alpha olefins having n carbon atoms comprising the steps of (a) dimerizing a linear alpha olefin having n carbon atoms in the presence of a dimerization catalyst to produce a linear internal olefin having 2n carbon atoms; (b)(i) reacting the linear internal olefin having 2n carbon atoms produced in step (a) with a trialkylaluminium compound in the presence of a catalytic amount of an isomerization/displacement catalyst in order to cause isomerization of the linear internal olefin and to displace alkyl group(s) from said trialkylaluminium compound to form an alkyl aluminium compound wherein at least one of the alkyl groups bound to aluminium is a linear alkyl which has been derived from the isomerization of said linear internal olefin; and (b)(ii) reacting said alkyl aluminium compound with an alpha olefin optionally in the presence of a displacement catalyst so as to displace said linear alkyl from said alkyl aluminium compound to form a linear alpha olefin having 2n carbon atoms.

19 Claims, No Drawings

U.S. PATENT DOCUMENTS

| | | | |
|---|---|---|---|
| 6,534,691 B2 | 3/2003 | Culver et al. | 585/527 |
| 6,545,108 B1 | 4/2003 | Moody et al. | 526/161 |
| 6,548,672 B1 | 4/2003 | Gibson et al. | 546/12 |
| 6,555,723 B2 | 4/2003 | Schiffino | 585/521 |
| 6,559,091 B1 | 5/2003 | Moody et al. | 502/167 |
| 6,559,252 B1 | 5/2003 | Horton et al. | 526/160 |
| 6,566,118 B1 | 5/2003 | Atkinson et al. | 435/239 |
| 6,657,026 B1 | 12/2003 | Kimberley et al. | 526/161 |
| 6,677,267 B2 | 1/2004 | Berardi et al. | 502/155 |
| 6,683,141 B1 | 1/2004 | Gibson et al. | 526/161 |
| 6,683,187 B2 | 1/2004 | De Boer et al. | 546/345 |
| 6,710,006 B2 | 3/2004 | De Boer et al. | 502/155 |
| 6,740,715 B2 | 5/2004 | Brookhart, III et al. | 526/161 |
| 6,803,432 B2 | 10/2004 | Bennett et al. | 526/161 |
| 6,825,297 B1 | 11/2004 | Devore et al. | 526/172 |
| 6,841,693 B1 | 1/2005 | Watanabe et al. | 556/32 |
| 2001/0000519 A1 | 4/2001 | Bennett | 526/329 |
| 2001/0016634 A1 | 8/2001 | Ittel et al. | 526/172 |
| 2002/0013431 A1 | 1/2002 | Bennett | 526/90 |
| 2002/0016425 A1 | 2/2002 | De Boer et al. | 526/172 |
| 2002/0016521 A1 | 2/2002 | Culver et al. | 585/527 |
| 2002/0019575 A1 | 2/2002 | Schiffino | 585/520 |
| 2002/0028941 A1 | 3/2002 | De Boer et al. | 546/167 |
| 2002/0035031 A1 | 3/2002 | Berardi et al. | 502/171 |
| 2002/0128409 A1 | 9/2002 | De Boer et al. | 526/172 |
| 2003/0036615 A1 | 2/2003 | Brookhart, III et al. | 526/161 |
| 2003/0045752 A1 | 3/2003 | De Boer et al. | 562/545 |
| 2003/0050494 A1 | 3/2003 | Brookhart, III et al. | 556/138 |
| 2003/0119921 A1 | 6/2003 | De Boer et al. | 518/715 |
| 2003/0125195 A1 | 7/2003 | Britovsek et al. | 502/117 |
| 2003/0144514 A1 | 7/2003 | De Boer et al. | 546/12 |
| 2003/0195110 A1 | 10/2003 | Moody et al. | 502/150 |
| 2003/0225228 A1 | 12/2003 | Moody et al. | 526/172 |
| 2004/0054241 A1 | 3/2004 | Maas et al. | 585/324 |
| 2004/0116758 A1 | 6/2004 | De Boer et al. | 585/521 |
| 2004/0199035 A1 | 10/2004 | Karl et al. | 585/324 |
| 2005/0059786 A1 | 3/2005 | De Boer et al. | 526/161 |

OTHER PUBLICATIONS

Gibson Vernon C et al: "The nature of the active species of bis(imino) pyridyl cobalt ethylene polymerisation catalysts" Chemical Communications Chemcom, Royal Society of Chemistry, GB, No. 21, 2001, pp. 2252-2253, XP002196345 ISSN 1359-7345.

Small Brooke L. et al: "Iron-Based Catalysts with Exceptionally High Activities and Selectivities for Oligomerizationof Ethylene to Linear.Alpha-Olefins" Journal of the American Chemical Society, Washington, DC, US, vol. 120, No. 28 Jul. 22, 1998, pp. 7143-7144, XP002086898 ISSN:0002-7863.

Ittel Steven D et al: "Late-Metal Catalysts for Ethylene Homo- and Copolymerization" Chemical Reviews, American Chemical Society. Easton, US, vol. 100, No. 4, 2000, pp. 1169-1203, XP000993140.

Britovsek G J P et al: "Oligomerisation of Ethylene by Bis(imino)pyridyliron and -cobalt Complexes" Chemistry—a European Journal, VCH Publishers, US vol. 6, No. 12, 2000, pp. 2221-2231, XP000942739, ISSN 0947-6539.

Britovsek G J P et al: "Novel olefin polymerization catalysts based on iron and cobalt" Chemical Communications—Chemcom, Royal Society of Chemistry, GB No. 7, 1998, pp. 849-850, XP002086893 ISSN 1359-7345.

D. Vogt, Oligomerisation of Ethylene to Higher Alpha-Olefins in Applied Homogeneous Catalysis with Organometallic Compounds, Ed. B. Cornills, W.A. Hermann, 2nd Edition, vol. 1, Ch. 23.1.1, p. 240-253, Wiley-VCH 2002.

D. van Leusen and B. Hessen, "1,1' Diisocyanoferrocene and a Convenient Synthesis of Ferrocenylamine" Organometallics, 2001, 20, pp. 224-226.

Chemical Abstracts, vol. 134, Columbus, Ohio, US; Abstract No. 231149, Radecka-Paryzek, W. et al., "Metal-Ion-Directed Synthesis of Homo- and Heteronuclear Dimetallic Schiff Base Podates," Polish J. Chem. 2001, 75(1), pp. 35-42.

T. Martijn Kooistra et al., Olefin Polymerizatino With [{bis(imino)pyridyl}CO"Cl$_2$]: Generation of the Active Species Involves Co$^I$ Angewandte Chemie. International Edition, Wiley-VCH, Weinheim, DE, vol. 40, No. 24, Dec. 17, 2001, pp. 4719-4722.

D. Vogt, "Oligomerization of Ethylene to Higher a-olefins" Ed. B. Cornils, W.A. Hermann vol. 1, Ch. 2.3.1.3, p. 245-258, VCH 1996.

Lions, Francis et al. "Tridentate Chelate Compounds. I" J. Am. Chem. Soc. (1957), vol. 79, 2733-38.

Figgins, Paul et al., "Complexes of Iron(II), Co(II), and Ni(II) with Biacetyl-bis-methylimine, 2-Pyridinal-methylimine and 2,6-Pyridinal-bis-methylimine," J. Am. Chem. Soc. (1960), vol. 82, pp. 820-824.

Brooke L. Small, "Tridentate Cobalt Catalysts for Linear Dimerization and Isomerization of α-Olefins," Organometallics 2003, 22, pp. 3178-3183.

Alison M. A. Bennett, "Novel, Highly Active Iron and Cobalt Catalysts for Olefin Polymerization", Chemtech, Jul. 1999, vol. 29, No. 7, pp. 24-28.

Brooke L. Small and Maurice Brookhart, "Polymerization of Propylene by a New Generation of Iron Catalysts: Mechanisms of Chain Initiation, Propagation, and Termination," Macromolecules 1999, vol. 32, No. 7, pp. 2120-2130.

Daan van Leusen and Bart Hessen, "1,1'-Diisocyanoferrocene and a Convenient Synthesis of Ferrocenylamine," Organometallics 2001, 20, pp. 224-226.

U.S. Appl. No. 11/088,023, filed Mar. 23, 2005, De Boer et al.
U.S. Appl. No. 11/080,170, filed Mar. 15, 2005, De Boer et al.
International Search Report for PCT/EP2005/053352 of Nov. 25, 2005.
Written Opinion for PCT/EP2005/053352 of Nov. 25, 2005.

PROCESS FOR PREPARING LINEAR ALPHA OLEFINS

FIELD OF THE INVENTION

The present invention relates to a process for preparing linear alpha olefins including a dimerization reaction.

BACKGROUND OF THE INVENTION

Higher alpha olefins having 6 or more carbon atoms are important as comonomers in polyolefins and as intermediates for detergent compounds. For example, 1-hexene and 1-octene are used as comonomers in LLDPE (linear low density polyethylene) and 1-decene is used as a starting material for the production of synthetic lubricants. However, there have hitherto only been general methods, and not targeted syntheses, for preparing most of these higher alpha olefins. These general methods tend to produce mixtures of the desired higher alpha olefins with other olefinic products, e.g. internal olefins. For example, the dehydrogenation of higher paraffins leads to a mixture of olefins which mostly contain internal double bonds. As another example, olefins having a relatively high number of carbon atoms and terminal double bonds can be prepared by the oligomerization of ethylene using transition metal catalysts, for example, by the Ziegler process, the SHOP process of Shell or the Ethyl Process. However, the mixtures obtained have to be separated sometimes by very complicated methods if a particular alpha olefin is to be isolated. In addition, ethylene is a very expensive feedstock material which results in a higher price for alpha olefins obtained by oligomerization.

For these reasons it would be desirable to provide a process for producing alpha olefins in a targeted manner from starting materials other than ethylene.

U.S. Pat. No. 5,124,465 and U.S. Pat. No. 5,191,145 disclose a process for preparing linear higher alpha olefins by successive transalkylation reactions. In these publications, a linear, internal olefin having from 4 to 30 carbon atoms or a mixture of such olefins is reacted with trialkylaluminium in the presence of an isomerization catalyst. This results in the formation of a trialkylaluminium compound in which at least one of the alkyl radicals is derived from the olefin used. This radical is present as a linear alkyl radical derived from the alpha olefins which has been formed by isomerization. The trialkylaluminium compound is subsequently reacted with an alpha-olefin in a displacement reaction in which the linear alpha-olefin which was bound to the aluminium is liberated. This process allows internal olefins to be isomerised effectively and in good yields to produce terminal olefins. However, the process is a pure isomerization reaction which does not make it possible to increase the chain length. The internal olefins used for the isomerization come from the usual sources and a targeted synthesis of alpha olefins having a desired chain length is not possible by means of the process.

U.S. 2004/0199035 and U.S. 2004/0054241 (BASF) relate to processes for preparing higher alpha olefins by a combination of isomerising transalkylation reactions with metathesis reactions. However, in order to make 1-octene from transalkylation/metathesis methods, it is necessary to start from 1-pentene. It would be desirable to produce 1-octene from 1-butene since 1-butene (present in Raffinate-II which is described below) is a relatively cheap and abundant feedstock compared to 1-pentene.

It would be desirable to provide methods for producing higher alpha olefins in a selective manner and, which, particularly for cost reasons, makes use of feedstocks other than ethylene, particularly relatively cheap feedstocks such as Raffinate (II) which contains a mixture of 1-butene and 2-butene.

SUMMARY OF THE INVENTION

According to one aspect of the present invention there is provided a process for the preparation of linear alpha olefins having 2n carbon atoms from linear alpha olefins having n carbon atoms comprising the steps of:
  (a) dimerizing a linear alpha olefin having n carbon atoms in the presence of a dimerization catalyst to produce a linear internal olefin having 2n carbon atoms;
  (b)(i) reacting the linear internal olefin having 2n carbon atoms produced in step (a) with a trialkylaluminium compound in the presence of a catalytic amount of an isomerization/displacement catalyst in order to cause isomerization of the linear internal olefin and to displace alkyl group(s) from said trialkylaluminium compound to form an alkyl aluminium compound wherein at least one of the alkyl groups bound to aluminium is a linear alkyl which has been derived from the isomerization of said linear internal olefin, and
  (b)(ii) reacting said alkyl aluminium compound with an alpha olefin optionally in the presence of a displacement catalyst so as to displace said linear alkyl from said alkyl aluminium compound to form a linear alpha olefin having 2n carbon atoms.

The process of the present invention advantageously produces linear alpha olefins in high yield and selectivity in a targeted manner.

DETAILED DESCRIPTION OF THE INVENTION

The process of the present invention comprises a dimerization reaction (step (a)) and a transmerization reaction (steps b(i) and b(ii)).

As used herein the term "transmerization" means a reaction which comprises step (b)(i) and step (b)(ii) as defined herein. In general terms, the term "transmerization" means a process that combines isomerization and transalkylation steps and which produces linear alpha olefins from linear internal olefins.

As used herein the term "dimerization" means a reaction by which an olefin containing n carbon atoms is converted to an olefin containing 2n carbon atoms.

The starting alpha olefin for use in the process of the present invention may be any alpha olefin having n carbon atoms. Preferably, n is an integer in the range from 3 to 11, more preferably in the range from 4 to 6. The starting alpha olefin used in the present process can be linear or branched. Preferably the starting alpha olefin is linear. Examples of starting alpha olefins which can be used in the present process are propene, 1-butene, 1-pentene and 1-hexene.

In a preferred embodiment herein the starting alpha olefin is 1-butene. When 1-butene is used as the starting alpha olefin, 1-octene is the alpha olefin produced by the process of the present invention. Possible sources of 1-butene are olefin mixtures which comprise 1-butene and 2-butene and possibly isobutene together with butanes. These are obtained, for example, in various cracking processes such as steam cracking or fluid catalytic cracking as C4 fraction. As an alternative, it is possible to use butene mixtures as are obtained in the dehydrogenation of butanes, by dimerization of ethene or in a Fischer-Tropsch reaction. Butanes present in the C4 fraction behave as inerts. Dienes, alkynes or enynes present in the mixtures can be removed by means of customary methods such as extraction or selective hydrogenation.

Since olefin-containing C4 hydrocarbon mixtures are available at a favourable price, the use of these mixtures improves the addition of value to steam cracker by-products. Furthermore, products with high added value are obtained.

The C4 fraction is most preferably used herein in the form of raffinate II, with the C4 stream being freed of interfering impurities, in particular oxygen compounds, by appropriate treatment over guard beds, preferably over high surface area aluminium oxides and/or molecular sieves. Raffinate II is obtained from the C4 fraction by firstly extracting butadiene and/or subjecting the stream to a selective hydrogenation. Removal of isobutene then gives the raffinate II.

Another source of the starting alpha olefin is a mixture which has been obtained by isomerizing the alpha olefin, such as a mixture of alpha olefin and internal olefin of the same carbon skeleton, e.g. 1-butene and 2-butene. The content of alpha olefin e.g. 1-butene in the isomerate may be increased by separation of at least some of the internal olefin e.g. 2-butene, such as by distillation. Another example of such a source, which may be equilibrium or non equilibrium mixtures of alpha and corresponding internal olefins e.g. 1-butene and 2-butene, is the unreacted linear olefin stream from a catalytic dimerization, e.g. dimerization step (a) optionally after isomerization and/or partial separation of internal olefin (see below).

The alpha olefin reacted in dimerization step (a) may be the same or different from the alpha olefin used as displacement alpha olefin in back displacement step b(ii). Using different olefins for the 2 steps can make separation of byproducts from one or both reactions easier, as the byproducts from, e.g. reactions when 1-butene is used in step (a) and propene is used in step b(ii), are of different carbon number and hence likely to be easier to separate by distillation, than is likely to be the case when the same olefin is used in both steps. However using the same olefin in both steps has the advantage of simplicity of separation.

It is also envisaged that mixtures of linear alpha olefins can be used as the starting olefin, including mixtures of odd and even-numbered olefins (e.g. a mixture of 1-butene and 1-pentene). Where the starting olefin is a mixture of olefins, some co-dimerization can take place in addition to dimerization. For example, in the case of a mixture of 1-butene and 1-pentene, the reaction products could be a mixture of a linear internal octene (from the dimerization of 1-butene), a linear internal decene (from the dimerization of 1-pentene) and a linear internal nonene (from the co-dimerization of 1-butene and 1-pentene).

Hence according to a further aspect of the present invention there is provided a process for the preparation of a linear alpha olefin having (n1+n2) carbon atoms comprising the steps of:

(a) co-dimerizing a linear alpha olefin having n1 carbon atoms with a linear alpha olefin having n2 carbon atoms in the presence of a dimerization catalyst to produce a linear internal olefin having (n1+n2) carbon atoms;

(b)(i) reacting the linear internal olefin having (n1+n2) carbon atoms produced in step (a) with a trialkylaluminium compound in the presence of a catalytic amount of an isomerization/displacement catalyst in order to cause isomerization of the linear internal olefin and to displace alkyl group(s) from said trialkylaluminium compound to form an alkyl aluminium compound wherein at least one of the alkyl groups bound to aluminium is a linear alkyl which has been derived from the isomerization of said linear internal olefin having (n1+n2) carbon atoms, and (b)(ii) reacting said alkyl aluminium compound with an alpha olefin optionally in the presence of a displacement catalyst so as to displace said linear alkyl from said alkyl aluminium compound to form a linear alpha olefin having (n1+n2) carbon atoms.

Preferably, n1 and n2 are different and are each integers in the range of from 3 to 11, more preferably in the range of from 4 to 6.

Dimerization

The process of the present invention comprises a dimerization step (step (a)). In the dimerization step a linear alpha olefin having n carbon atoms is dimerized in the presence of a dimerization catalyst to produce a linear internal olefin having 2n carbon atoms.

Alternatively, as mentioned above, the process of the present invention comprises a co-dimerization step. The same process conditions, dimerization catalysts and the like can be used for a co-dimerization reaction as are described below for use in a dimerization reaction.

Any suitable dimerization catalyst known to those skilled in the art can be used in the process herein, provided it is highly selective to the production of linear internal olefins. Preferred dimerization catalysts for use herein are those which produce at least 80%, preferably at least 90%, more preferably at least 95% of linear internal olefins, such percentages being by weight of final product produced from the dimerization of a starting linear alpha olefin.

Suitable dimerization catalysts for use herein comprise transition metal complexes based on a transition metal atom and a bis-arylimine pyridine bidentate ligand, such as those disclosed in Shell patent publications U.S. Pat. Nos. 6,710,006, 6,683,187, US 2005/0059786, US 2003/0119921 and co-pending U.S. patent application Ser. No. 11/088,023, filed Mar. 23, 2005, the disclosures of which are herein incorporated by reference in their entirety. Other transition metal complexes suitable for use as dimerization catalysts include those disclosed in U.S. Pat. No. 6,291,733 B1 (Chevron) which is herein incorporated by reference in its entirety.

Other suitable dimerization catalysts for use herein include titanium bisamide compounds such as those disclosed in US 2003/0045752 which is herein incorporated by reference in its entirety.

Preferred catalyst compositions for use in the dimerization step (a) of the present invention are those of the type disclosed in co-pending U.S. patent application Ser. No. 11/088,023, filed Mar. 23, 2005, which is herein incorporated by reference in its entirety. Such catalyst compositions comprise one or more transition metal complexes, the transition metal complexes each comprising a transition metal atom complexed with a bis-arylimine pyridine ligand of formula (I) below:

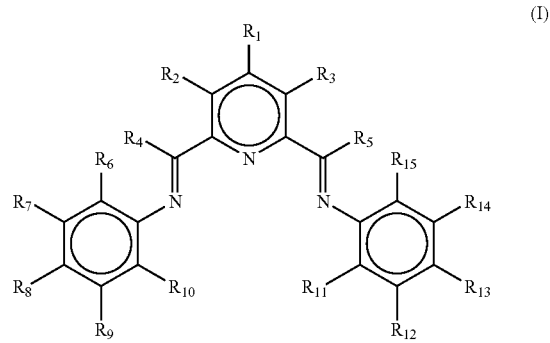

wherein $R_1$-$R_5$, $R_7$-$R_9$, $R_{12}$ and $R_{14}$ are each, independently, hydrogen, optionally substituted hydrocarbyl, an inert functional group, or any two of $R_1$-$R_3$ and $R_7$-$R_9$ vicinal to one another taken together may form a ring, $R_6$ is hydrogen, optionally substituted hydrocarbyl, an inert functional group, or taken together with $R_7$ or $R_4$ to form a ring, $R_{10}$ is hydrogen, optionally substituted hydrocarbyl, an inert functional group, or taken together with $R_9$ or $R_4$ to form a ring, $R_{11}$ is hydrogen, optionally substituted hydrocarbyl, an inert functional group, or taken together with $R_{12}$ or $R_5$ to form a ring, $R_{15}$ is hydrogen, optionally substituted hydrocarbyl, an inert functional group, or taken together with $R_{14}$ or $R_5$ to form a ring, provided that $R_{13}$ and at least one of $R_{12}$ and $R_{14}$ are independently selected from optionally substituted $C_1$-$C_{30}$ alkyl, optionally substituted $C_4$-$C_{30}$ alkyloxy, halogen and optionally substituted $C_5$-$C_{20}$ aryl or $R_{13}$ taken together with $R_{12}$ or $R_{14}$ form a ring, or $R_{12}$ taken together with $R_{11}$ form a ring and $R_{14}$ taken together with $R_{15}$ form a ring. Preferably especially for catalyst systems soluble in chemically inert non-polar solvents (see further below) $R_{13}$ and at least one of $R_{12}$ and $R_{14}$ are independently selected from optionally substituted $C_1$-$C_{30}$ alkyl, optionally substituted $C_4$-$C_{30}$ alkyloxy and optionally substituted $C_5$-$C_{20}$ aryl, provided that at least one of $R_{12}$, $R_{13}$ and $R_{14}$ is optionally substituted $C_4$-$C_{30}$ alkyloxy.

One class of transition metal complexes suitable as catalyst precursors for use in the dimerization step herein are bis-arylimine pyridine $MX_n$ complexes which comprise a bis-arylimine pyridine ligand of formula (I) above, wherein M is a transition metal atom and n matches the formal oxidation state of transition metal atom M and is preferably 1, 2 or 3; and X is halide, optionally substituted hydrocarbyl (e.g. $CH_3$, neopentyl and $CH_2$-Ph), C1-C6 alkoxide, amide, or hydride. Particularly preferred X groups are halide, especially chlorine.

Transition metals for use in the transition metal complexes herein are preferably selected from any Group 4 to Group 10 transition metal, more preferably Ti, V, Cr, Mn, Fe, Co, Ni, Pd, Rh, Ru, Mo, Nb, Zr, Hf, Ta, W, Re, Os, Ir and Pt, even more preferably Ti, V, Cr, Mn, Fe, Co, Ni, Pd and Pt, especially Fe, Co and Cr. The preferred transition metal for use in the dimerization catalyst herein is Co.

Bis-arylimine pyridine $MX_n$ complexes can be reacted with a non-coordinating anion generating species to form a cationic complex having the formula [bis-arylimine pyridine $MX_p$]$^+$[NC$^-$]$_p$ comprising a bis-arylimine pyridine ligand having formula (I) above, wherein M and X are as defined above, NC$^-$ is a non-coordinating anion; and p+q matches the formal oxidation state of transition metal atom M. Preferably p+q is 2 or 3.

By the term "non-coordinating anion" is meant an anion which does not substantially coordinate to the metal atom M. Non-coordinating anions (NC$^-$) that may be suitably employed include bulky anions such as tetrakis [3,5-bis(trifluoromethyl)phenyl]borate (BAF$^-$), $(C_6F_5)_4B^-$, and anions of alkylaluminium compounds including $R_3AlX'^-$, $R_2AlClX'^-$, $RAlCl_2X'^-$, and "$RAlOX'^-$", wherein R is hydrogen, optionally substituted hydrocarbyl (e.g. C1-C20 alkyl or aryl), or an inert functional group, and X' is halide, especially chlorine or fluorine, C1-C20 alkoxide or aryloxide (eg. phenoxide and substituted aryl oxides such as 2,4,6-trimethylphenyloxide, 2,4,6-tributylphenyloxide) or oxygen. A preferred non-coordinating anion for use herein is tetrakis [3,5-bis(trifluoromethyl)phenyl]borate (BAF$^-$).

In a preferred embodiment of the invention, $R_{13}$ and at least one of $R_{12}$ and $R_{14}$ are independently selected from optionally substituted $C_1$-$C_{30}$ alkyl, optionally substituted $C_4$-$C_{30}$ alkyloxy, optionally substituted $C_5$-$C_{20}$ aryl with the proviso that at least one of $R_{12}$, $R_{13}$ and $R_{14}$ is optionally substituted $C_4$-$C_{30}$ alkyloxy.

In one class of bis-arylimine pyridine transition metal complexes, the bis-arylimine pyridine ligand having formula (I) above, is such that $R_8$ and at least one of $R_7$ and $R_9$ are independently selected from optionally substituted $C_1$-$C_{30}$ alkyl, optionally substituted $C_4$-$C_{30}$ alkyloxy, halogen and optionally substituted $C_5$-$C_{20}$ aryl, or $R_8$ taken together with $R_7$ or $R_9$ form a ring, or $R_7$ taken together with $R_6$ form a ring and $R_9$ taken together with $R_{10}$ form a ring with the proviso that at least one of $R_7$, $R_8$ and $R_9$ is optionally substituted $C_4$-$C_{30}$ alkyloxy. Preferably $R_8$ and at least one of $R_7$ and $R_9$ are independently selected from optionally substituted $C_4$-$C_{30}$ alkyl, optionally substituted $C_4$-$C_{30}$ alkyloxy and optionally substituted $C_5$-$C_{20}$ aryl.

It will be immediately apparent to the person skilled in the art, that when $R_8$ and at least one of $R_7$ and $R_9$ are independently selected from optionally substituted $C_4$-$C_{30}$ alkyl, optionally substituted $C_4$-$C_{30}$ alkyloxy and optionally substituted $C_5$-$C_{20}$ aryl with the proviso that at least one of $R_7$, $R_8$ and $R_9$ is optionally substituted $C_4$-$C_{30}$ alkyloxy, it is not possible for $R_8$ to be independently, hydrogen, optionally substituted hydrocarbyl, an inert functional group, or any two of $R_7$-$R_9$ vicinal to one another taken together to form a ring.

The term "Hydrocarbyl group" as used herein means a group containing only carbon and hydrogen atoms. Unless otherwise stated, the number of carbon atoms is preferably in the range from 1 to 30, especially from 1 to 8. Unless otherwise stated, the hydrocarbyl group may be saturated or unsaturated, aliphatic, cycloaliphatic or cycloaromatic (e.g. phenyl), but is preferably aliphatic. Suitable hydrocarbyl groups include primary, secondary and tertiary carbon atom groups such as those described below.

The phrase "optionally substituted hydrocarbyl" as used herein is used to describe hydrocarbyl groups which may optionally contain one or more "inert" heteroatom-containing functional groups. By "inert" it is meant that the functional groups do not interfere to any substantial degree with the catalytic process in which the transition metal complex may be employed. Non-limiting examples of such inert groups are halides, such as fluoride and chloride, silanes, stannanes, ethers, alkoxides and amines with adequate steric shielding, all well-known to those skilled in the art. Some examples of such groups include methoxy, trimethylsiloxy and eicosanoxy. Said optionally substituted hydrocarbyl may include primary, secondary and tertiary carbon atom groups of the nature described below.

The term "inert functional group" as used herein means a group other than optionally substituted hydrocarbyl which is inert under the reaction conditions for any reaction or process in which the transition metal complex may be employed. By "inert" it is meant that the functional group does not interfere to any substantial degree with the catalytic process in which the transition metal complex may be employed. Examples of inert functional groups suitable for use herein include halides, ethers, and amines such as tertiary amines. Preferably the inert functional group is a halide, especially fluorine and chlorine.

The term "Primary carbon atom group" as used herein means a —$CH_2$—R group wherein R is selected from hydrogen, an optionally substituted hydrocarbyl (preferably selected from $C_1$-$C_6$ alkyl, phenyl, and $C_1$-$C_6$ alkoxy or aryloxy (e.g. OPh)), or an inert functional group (preferably selected from fluorine, chlorine and —$N(C_1$-$C_6$ alkyl)$_2$). Examples of suitable primary carbon atom groups include, but are not limited to, —$CH_3$, —$C_2H_5$, —$CH_2Cl$, —CH$_2$OCH$_3$, —CH$_2$N(C$_2$H$_5$)$_2$, —CH$_2$—C(CH$_3$)$_3$, —CH$_2$—O-Ph and —CH$_2$Ph. Unless otherwise stated, preferred primary carbon atom groups for use herein are those wherein R is selected from hydrogen or a C$_1$-C$_6$ unsubstituted hydrocarbyl, preferably wherein R is selected from hydrogen, C$_1$-C$_6$ alkyl and phenyl, more preferably wherein R is hydrogen or a C$_1$-C$_3$ alkyl.

The term "Secondary carbon atom group" as used herein means a —CH(R)$_2$ group wherein each R is independently selected from an optionally substituted hydrocarbyl (preferably selected from a C$_1$-C$_6$ alkyl, C$_1$-C$_6$ alkoxy or aryloxy (eg. OPh) and phenyl), or an inert functional group (preferably selected from fluorine and chlorine). Alternatively, the two R groups may together represent a double bond moiety, e.g. =CH$_2$, or a cycloalkyl group, e.g. cyclohexyl. Examples of secondary carbon atom groups include, but are not limited to, —CH(CH$_3$)$_2$, —CHCl$_2$, —CHPh$_2$, —CH=CH$_2$ and cyclohexyl. Unless otherwise stated, preferred secondary carbon atom groups for use herein are those in which R is a C$_1$-C$_6$ unsubstituted hydrocarbyl preferably a C$_1$-C$_6$ alkyl, more preferably a C$_1$-C$_3$ alkyl.

The term "Tertiary carbon atom group" as used herein means a —C(R)$_3$ group wherein each R is independently selected from an optionally substituted hydrocarbyl (preferably selected from C$_1$-C$_6$ alkyl and C$_1$-C$_6$ alkoxy), or an inert functional group (preferably selected from chlorine and fluorine). Alternatively, the three R groups may together represent a triple bond moiety, e.g. —C≡CPh, or a ring system containing tertiary carbon atoms such as adamantyl derivatives. Examples of tertiary carbon atom groups include, but are not limited to, —C(CH$_3$)$_3$, —CCl$_3$, —C≡CPh, 1-Adamantyl and —C(CH$_3$)$_2$(OCH$_3$). Unless otherwise stated, preferred tertiary carbon atom groups for use herein are those wherein each R is a C$_1$-C$_6$ unsubstituted hydrocarbyl group, preferably wherein each R is a C$_1$-C$_6$ alkyl group, more preferably a C$_1$-C$_3$ alkyl group, even more preferably wherein each R is methyl. In the case wherein each R is a methyl group, the tertiary carbon atom group is tert-butyl.

The rings which may be formed by any two of R$_1$-R$_3$ and R$_7$-R$_9$ vicinal to one another taken together, R$_6$ taken together with R$_7$, R$_{10}$ taken together with R$_9$, R$_{11}$ taken together with R$_{12}$ and R$_{15}$ taken together with R$_{14}$, are preferably optionally substituted C$_5$-C$_{20}$ cyclic hydrocarbyl groups, more preferably optionally substituted C$_5$-C$_{20}$ cycloaliphatic or polycycloaliphatic groups or optionally substituted C$_5$-C$_{20}$ aromatic or polyaromatic groups, even more preferably optionally substituted C$_5$-C$_8$ cycloaliphatic or aromatic groups, especially a C$_6$ cycloaliphatic or aromatic groups, especially benzene. Suitable optional substituents are any suitable substituents known to those skilled in the art, preferably halide (e.g. F, Cl), C$_1$-C$_6$ alkoxy (e.g. OCH$_3$) and C$_1$-C$_6$ alkyl groups (e.g. —CH$_3$, t-butyl).

The rings which may be formed by R$_{13}$ taken together with R$_{12}$ or R$_{14}$, and, where applicable, R$_8$ taken together with R$_7$ or R$_9$ are preferably optionally substituted C$_5$-C$_{20}$ cyclic hydrocarbyl groups, more preferably optionally substituted C$_5$-C$_{20}$ cycloaliphatic or polycycloaliphatic groups or optionally substituted C$_5$-C$_{20}$ aromatic or polyaromatic groups, even more preferably optionally substituted C$_5$-C$_{10}$ cycloaliphatic or aromatic groups, even more preferably optionally substituted C$_5$-C$_8$ cycloaliphatic or aromatic groups, especially C$_5$ and C$_6$ cycloaliphatic or aromatic groups, especially benzene. Suitable optional substituents are any suitable substituents known to those skilled in the art, preferably halide (e.g. F, Cl), C$_1$-C$_6$ alkoxy (e.g. —OCH$_3$) and C$_1$-C$_6$ alkyl groups (e.g. —CH$_3$, t-butyl).

The rings which may be formed by R$_6$ taken together with R$_4$, R10 taken together with R$_4$, R$_{11}$ taken together with R$_5$ and R$_{15}$ taken together with R$_5$, are preferably optionally substituted nitrogen-containing cyclic groups containing from 4 to 20 carbon atoms and at least one nitrogen atom, more preferably optionally substituted nitrogen-containing cycloaliphatic groups containing from 4 to 20 carbon atoms atoms and at least one nitrogen atom, even more preferably optionally substituted nitrogen-containing cycloaliphatic groups containing 4 to 5 carbon atoms and at least one nitrogen atom. Suitable optional substituents are any suitable substituents known to those skilled in the art, preferably halide (e.g. F, Cl), C1-C6 alkoxy (e.g. —OCH$_3$) and C1-C6 alkyl groups (e.g. —CH$_3$, t-butyl).

In preferred embodiments herein, none of the R1-R15 groups form rings with each other. Hence in formula I above it is preferred that R1-R12 and R14 are each independently selected from hydrogen, optionally substituted hydrocarbyl groups such as the primary, secondary and tertiary carbon atoms groups defined above and inert functional groups such as halide; with the proviso that R$_{13}$ and at least one of R$_{12}$ and R$_{14}$ are independently selected from optionally substituted C$_1$-C$_{30}$ alkyl, optionally substituted C$_4$-C$_{30}$ alkyloxy and optionally substituted C$_5$-C$_{20}$ aryl and further provided that at least one of R$_{12}$, R$_{13}$ and R$_{14}$ is optionally substituted C$_4$-C$_{30}$ alkyloxy.

The term "optionally substituted C$_1$-C$_{30}$ alkyl" in relation to the R$_{12}$, R$_{13}$ and R$_{14}$ groups, and, where applicable, the R$_7$, R$_8$ and R$_9$ groups of formula (I) above means a C$_1$ to C$_{30}$ linear or branched alkyl group, which may be substituted with one or more "inert" functional groups known to those skilled in the art, in particular a halide, preferably fluorine. Preferred optionally substituted alkyl groups comprise from 3 to 25 carbon atoms, more preferably from 4 to 20 carbon atoms. Preferably, the alkyl group is an unsubstituted alkyl group. Examples of suitable "optionally substituted C$_1$-C$_{30}$ alkyl" include octadecyl, tetradecyl, dodecyl, decyl, octyl, hexyl, pentyl, tert-butyl and iso-propyl, especially tert-butyl and iso-propyl.

The term "optionally substituted C$_4$-C$_{30}$ alkyloxy" in relation to the R$_{12}$, R$_{13}$ and R$_{14}$ groups, and, where applicable, the R$_7$, R$_8$ and R$_9$ groups of formula (I) above means a C$_4$-C$_{30}$ optionally substituted alkyl group which is attached to an oxygen atom, the alkoxy group being attached to the aryl group of the bis-aryl imine pyridine backbone via the oxygen atom. Preferably, the optionally substituted alkyloxy group comprises from 6 to 30 carbon atoms, more preferably from 8 to 30 carbon atoms, and most preferably from 10 to 25 carbon atoms. Preferably, the alkyloxy group is an unsubstituted alkyloxy group. Examples of suitable "optionally substituted C$_4$-C$_{30}$ alkyloxy" include eicosanoxy, octadecyloxy, hexadecyloxy, tetradecyloxy, dodecyloxy, decyloxy, hexyloxy, pentyloxy, butyloxy and tert-butyloxy, especially eicosanoxy, dodecyloxy, pentyloxy and tert-butyloxy. A particularly preferred optionally substituted C4-C30 alkyloxy group is eicosanoxy.

The term "optionally substituted C$_5$-C$_{20}$ aryl" in relation to the R$_{12}$, R$_{13}$ and R$_{14}$ groups, and, where applicable, the R$_7$, R$_8$ and R$_9$ groups of formula (I) above means an aryl or heteroaryl group, comprising from 5 to 20 ring atoms and wherein one or more of the ring atoms can be substituted with one or more substituents known to those skilled in the art, preferably selected from optionally substituted hydrocarbyl, preferably C$_1$-C$_6$ alkyl, preferably methyl, and "inert" functional groups, such as halide. In a heteroaryl group, one or more of the ring atoms is a heteroatom, such as nitrogen, oxygen or sulfur, provided that the heteroatom is inert with regard to the catalytic process in which the transition metal complex is employed. Preferably the heteroaryl groups are aromatic, fully substituted or the heteroatom is fully shielded from the transition metal atom. Preferred heteroaryl groups are 1-pyrrolyl groups. Preferably all of the ring atoms are carbon atoms.

Within the term "optionally substituted $C_5$-$C_{20}$ aryl" is encompassed mono- and poly-aromatic groups. Preferred optionally substituted $C_5$-$C_{20}$ aryl groups comprise from 5 to 10 ring carbon atoms, more preferably 5 or 6 ring carbon atoms. Preferably, the aryl groups are unsubstituted aryl groups, including 1-pyrrolyl groups. Most preferred are optionally substituted phenyl groups, especially phenyl.

In one class of transition metal complexes herein, $R_{13}$ and at least one of $R_{12}$ and $R_{14}$ are independently selected from optionally substituted $C_4$-$C_{30}$ alkyl, optionally substituted $C_4$-$C_{30}$ alkyloxy and optionally substituted $C_5$-$C_{20}$ aryl, with the proviso that at least one of $R_{12}$, $R_{13}$ and $R_{14}$ is optionally substituted $C_4$-$C_{30}$ alkyloxy, and $R_8$ and at least one of $R_7$ and $R_9$ are independently selected from optionally substituted $C_4$-$C_{30}$ alkyl, optionally substituted $C_4$-$C_{30}$ alkyloxy and optionally substituted $C_5$-$C_{20}$ aryl, with the proviso that at least one of $R_7$, $R_8$ and $R_9$ is optionally substituted $C_4$-$C_{30}$ alkyloxy.

In another class of transition metal complexes herein, $R_{12}$, $R_{13}$ and $R_{14}$ are all independently selected from optionally substituted $C_4$-$C_{30}$ alkyl, optionally substituted $C_4$-$C_{30}$ alkyloxy and optionally substituted $C_5$-$C_{20}$ aryl, with the proviso that at least one of $R_{12}$, $R_{13}$ and $R_{14}$ is optionally substituted $C_4$-$C_{30}$ alkyloxy.

In another class of transition metal complexes herein, $R_{12}$, $R_{13}$ and $R_{14}$ are all independently selected from optionally substituted $C_4$-$C_{30}$ alkyl, optionally substituted $C_4$-$C_{30}$ alkyloxy and optionally substituted $C_5$-$C_{20}$ aryl, with the proviso that at least one of $R_{12}$, $R_{13}$ and $R_{14}$ is optionally substituted $C_4$-$C_{30}$ alkyloxy.

Preferred transition metal complexes for use in the dimerization step of the present invention comprise ligands according to formula (I), in which the following R groups appear: $R_1$-$R_3$ are hydrogen; and/or $R_4$ and $R_5$ are methyl, hydrogen, benzyl or phenyl, preferably methyl, phenyl or hydrogen, more preferably methyl.

One preferred class of transition metal complexes comprises ligands according to formula (I), in which the following R groups appear: $R_{12}$ and $R_{14}$ are independently selected from $C_1$-$C_{30}$ alkyl and $C_5$-$C_{20}$ aryl, preferably $C_5$-$C_{20}$ aryl, more preferably phenyl; $R_{13}$ is $C_4$-$C_{30}$ alkyloxy, preferably $C_{10}$-$C_{25}$ alkyloxy, more preferably eicosanoxy.

Another preferred class of transition metal complexes comprise ligands according to formula (I), in which the following R groups appear: R7, R9, $R_{12}$ and $R_{14}$ are independently selected from $C_1$-$C_{30}$ alkyl and $C_5$-$C_{20}$ aryl, preferably $C_5$-$C_{20}$ aryl, more preferably phenyl; R8 and $R_{13}$ is $C_4$-$C_{30}$ alkyloxy, preferably $C_{10}$-$C_{25}$ alkyloxy, more preferably eicosanoxy.

Another preferred class of transition metal complexes comprise ligands according to formula (I), in which the following R groups appear: $R_{12}$ and $R_{14}$ are independently selected from $C_1$-$C_{30}$ alkyl and $C_5$-$C_{20}$ aryl, preferably $C_5$-$C_{20}$ aryl, more preferably phenyl; $R_{13}$ is $C_4$-$C_{30}$ alkyloxy, preferably $C_{10}$-$C_{25}$ alkyloxy, more preferably eicosanoxy; $R_6$ is a tertiary carbon atom group, preferably tert-butyl, and preferably R7-R10, R11 and R15 are hydrogen.

Another preferred class of transition metal complexes comprise ligands according to formula (I), in which the following R groups appear: $R_{12}$ and $R_{14}$ are independently selected from $C_1$-$C_{30}$ alkyl and $C_5$-$C_{20}$ aryl, preferably $C_5$-$C_{20}$ aryl, more preferably phenyl; $R_{13}$ is $C_4$-$C_{30}$ alkyloxy, preferably $C_{10}$-$C_{25}$ alkyloxy, more preferably eicosanoxy; $R_6$ is selected from $C_1$-$C_{30}$ alkyl, preferably $C_1$-$C_{10}$ alkyl, more preferably $C_3$-$C_6$ alkyl, most preferably tert-butyl or iso-propyl; $R_8$ and $R_{10}$ are hydrogen; and preferably $R_7$ and $R_9$ are hydrogen.

Another preferred class of transition metal complexes comprise ligands according to formula (I), in which the following R groups appear: $R_{12}$ and $R_{14}$ are independently selected from $C_1$-$C_{30}$ alkyl and $C_5$-$C_{20}$ aryl, preferably $C_5$-$C_{20}$ aryl, more preferably phenyl; $R_{13}$ is $C_4$-$C_{30}$ alkyloxy, preferably $C_{10}$-$C_{25}$ alkyloxy, more preferably eicosanoxy; $R_6$, $R_8$ and $R_{10}$ are each independently selected from a primary carbon atom group, preferably $C_1$-$C_6$ alkyl, more preferably methyl, and preferably R7, R9, R11 and R15 are hydrogen.

Another preferred class of transition metal complexes comprise ligands according to formula (I), in which the following R groups appear: $R_{12}$ and $R_{14}$ are independently selected from $C_1$-$C_{30}$ alkyl and $C_5$-$C_{20}$ aryl, preferably $C_5$-$C_{20}$ aryl, more preferably phenyl; $R_{13}$ is $C_4$-$C_{30}$ alkyloxy, preferably $C_{10}$-$C_{25}$ alkyloxy, more preferably eicosanoxy; $R_6$, $R_8$ and $R_{10}$ are independently selected from $C_1$-$C_{30}$ alkyl, preferably $C_1$-$C_{10}$ alkyl, more preferably $C_1$-$C_6$ alkyl, most preferably methyl, ethyl, iso-propyl or tert-butyl; and preferably $R_7$ and $R_9$ are hydrogen.

Another class of transition metal complexes comprise ligands according to formula (I), in which the following R groups appear: $R_7$ and $R_9$ are independently selected from $C_1$-$C_{30}$ alkyl and $C_5$-$C_{20}$ aryl, preferably $C_5$-$C_{20}$ aryl, more preferably phenyl; $R_8$ is $C_4$-$C_{30}$ alkyloxy, preferably $C_{10}$-$C_{25}$ alkyloxy, more preferably eicosanoxy.

In a preferred embodiment, the transition metal complex comprises a ligand according to formula (I), wherein $R_1$-$R_3$ are hydrogen, $R_4$ and $R_5$ are methyl, $R_6$, $R_8$ and $R_{10}$ are methyl, $R_7$, $R_9$, $R_{11}$ and $R_{15}$ are hydrogen, $R_{12}$ and $R_{14}$ are phenyl and $R_{13}$ is eicosanoxy.

In another preferred embodiment, the transition metal complex comprises a ligand according to formula (I), wherein $R_1$-$R_3$ are hydrogen, $R_4$ and $R_5$ are methyl, $R_6$, $R_{10}$, $R_{11}$ and $R_{15}$ are hydrogen, $R_7$, $R_9$, $R_{12}$ and $R_{14}$ are phenyl and $R_8$ and $R_{13}$ is eicosanoxy.

In another preferred embodiment, the transition metal complex comprises a ligand according to formula (I), wherein $R_1$-$R_3$ are hydrogen, $R_4$ and $R_5$ are methyl, $R_6$ is tert-butyl, $R_7$, $R_8$, $R_9$, $R_{10}$, $R_{11}$ and $R_{15}$ are hydrogen, $R_{12}$ and $R_{14}$ are phenyl and $R_{13}$ is eicosanoxy.

In another preferred embodiment, the transition metal complex comprises a ligand according to formula (I), wherein $R_1$-$R_3$ are hydrogen, $R_4$ and $R_5$ are methyl, $R_6$, $R_9$, $R_{12}$ and $R_{14}$ are hydrogen, $R_7$ and $R_{14}$ are iso-propyl, $R_{10}$ and $R_{11}$ are methyl and $R_8$ and $R_{13}$ is eicosanoxy.

The catalyst compositions for use in the dimerization step herein also preferably comprise at least one co-catalyst compound (b). The purpose of co-catalyst compound(s) is to form an activated catalyst system. In the case when a bis-arylimine pyridine $MX_n$ complex is present, the co-catalyst is selected from (1) a co-catalyst compound capable of abstracting an anion and transferring an optionally susbstituted hydrocarbyl or hydride group to the metal atom, or (2) a co-catalyst compound capable of abstracting an anion and a co-catalyst compound capable of transferring an optionally substituted hydrocarbyl or hydride group to the transition metal atom. In the case when a cationic [bis-arylimine pyridine $MX_p^+$] $[NC^-]_q$ complex is present, the co-catalyst compound is selected from a co-catalyst compound capable of transferring an optionally substituted hydrocarbyl or hydride group to the transition metal atom.

A co-catalyst compound capable of abstracting an anion ($X^-$ group) and transferring an optionally substituted hydrocarbyl or hydride group to the transition metal atom (M), preferably at a temperature in the range of $-100°$ C. to $+300°$ C., is selected from alkylaluminium compounds such as alkylaluminoxane and alkylaluminium halides. Preferred compounds of this type are methylaluminoxane (MAO) and modified methylaluminoxane (MMAO).

A co-catalyst compound capable of transferring an optionally substituted hydrocarbyl or hydride group to the transition metal atom (M), preferably at a temperature in the range of $-100°$ C. to $+300°$ C., is selected from alkylaluminium compounds such as alkyl aluminoxanes, alkyl lithium compounds, Grignards, alkyl tin and alkyl zinc compounds, such as diethyl zinc. Preferred compounds of this type are methylaluminoxane (MAO) and modified methylaluminoxane (MMAO).

A co-catalyst compound capable of abstracting an anion ($X^-$ group) from the transition metal atom (M), preferably at a temperature in the range of $-100°$ C. to $+300°$ C., is selected from strong neutral Lewis acids such as $SbF_5$, $BF_3$ and $Ar_3B$, wherein Ar is a strong electron-withdrawing aryl group such as $C_6F_5$ or $3,5-(CF_3)_2C_6H_3$ or from salts with non-coordinating anions ($NC^-$) such as tetrakis [3,5-bis(trifluoromethyl)-phenyl]borate ($BAF^-$), $(C_6F_5)_4B^-$, and anions of alkylaluminium compounds including $R_3AlX'^-$, $R_2AlClX'^-$, $RAlCl_2X'^-$, and "$RAlOX'^-$", wherein R is hydrogen, optionally substituted hydrocarbyl or an inert functional group, and X' is halide, alkoxide or oxygen. A preferred salt with a non-coordinating anion for use herein is sodium tetrakis [3,5-bis(trifluoromethyl)-phenyl]borate ($Na^+$ $BAF^-$).

Additional co-catalyst compounds (c), which may be used in addition to the co-catalyst compound(s) listed above, include, but are not necessarily limited to, neutral Lewis donor molecules.

The term "neutral Lewis donor molecule" as used in herein means a compound which may suitably act as a Lewis base, such as ethers, amines, sulphides and organic nitriles, for example, triethylamine or 2,6-di-tert-butylpyridine.

The ligands and transition metal complexes described hereinabove may be prepared using the chemical processes and equivalent processes to those illustrated in the examples of the present invention and any references therein, as well as the processes known from U.S. Pat. Nos. 6,710,006, 6,683, 187, US 2005/0059786, US 2003/0119921 and any references incorporated therein.

Catalyst systems based on the transition metal complexes described herein may be formed by mixing together the transition metal complex or a mixture of a transition metal salt and the appropriate bis-arylimine pyridine ligand of formula (I), co-catalyst compound(s) (b), and optionally one or more additional co-catalyst compounds (c), in any order.

Conveniently, the preparation of catalyst systems based on transition metal complexes described herein may be performed in the presence of the dimerization reaction mixture or in the presence of a chemically inert solvent which may be polar or non-polar. Preferably, the catalyst system is prepared in the presence of the reaction mixture or in the presence of a chemically inert non-polar solvent, more preferably in the presence of a chemically inert non-polar solvent.

The use of a chemically inert non-polar solvent in the preparation of the catalyst system for the dimerization step especially to provide a solution of that catalyst system may be desired for ease of handling, storage and use of the catalyst system, in particular for accurate dosing of the catalyst composition, especially during continuously operated reaction processes. Catalyst systems disclosed in the copending U.S. application Ser. No. 11/088,023, filed Mar. 23, 2005 mentioned above with transition metal complexes having ligands of formula I are especially preferred for use in such solutions. Examples of suitable chemically inert non-polar solvents include o-, m- or p-xylene, toluene, benzene, pentane, isopentane, heptane, cyclohexane and isooctane, preferably the solvent is toluene, isopentane, cyclohexane and isooctane, especially toluene and isooctane.

In one embodiment, the catalyst system for the dimerization step is formed by combining a solution of the transition metal complex dissolved in a chemically inert non-polar solvent with a solution of the co-catalyst compound(s) (b) and optionally additional co-catalyst compound(s) (c) in a chemically inert non-polar solvent. The combining of these two separate solutions may be performed either in the presence or the absence of the reactant composition.

Alternatively, the catalyst system for the dimerization is formed by combining a solution comprising a mixture of a transition metal salt and a bis-arylimine pyridine ligand of formula (I) dissolved in a chemically inert non-polar solvent with a solution of the co-catalyst compound(s) (b) and optionally additional co-catalyst compound(s) (c) in a chemically inert non-polar solvent. The combining of these two separate solutions may be performed either in the presence or the absence of the reactant composition.

In another embodiment, the catalyst system is formed by combining a solution of the transition metal bis-arylimine pyridine complex in a chemically inert non-polar solvent, with the co-catalyst compound(s) (b) and optionally additional co-catalyst compound(s) (c), which are present in the reaction media.

Alternatively, the catalyst system is formed by combining a mixture of a transition metal salt and a bis-arylimine pyridine ligand of formula (I) in a chemically inert non-polar solvent, with the co-catalyst compound(s) (b) and optionally additional co-catalyst compound(s) (c) which are present in the reaction media.

In another embodiment, the catalyst system is prepared by combining all the components of the catalyst system in a chemically inert non-polar solvent.

In another embodiment, the catalyst system for the dimerization is prepared by combining all the components of the catalyst system in the reaction media.

The dimerization reaction of the present invention may be conveniently carried out using the following conditions.

A quantity of the catalyst system is usually employed in the dimerization reaction mixture so as to contain from $10^{-3}$ to $10^{-9}$ gram atom of transition metal atom M per mole of feed olefin to be reacted.

The dimerization reaction may be most conveniently conducted over a range of temperatures from $-100°$ C. to $+200°$ C., preferably in the range of from $-50°$ C. to $150°$ C., more preferably in the range of from $-10°$ C. to $120°$ C., most preferably from $10°$ C. to $100°$ C., especially from $20°$ C. to $90°$ C.

The dimerization reaction may be conveniently carried out at a pressure of 0.01 to 15 MPa (0.1 to 150 bar(a)), more preferably 0.1 to 10 MPa (1 to 100 bar(a)), and most preferably 0.1 to 5 MPa (1 to 50 bar(a)).

The optimum conditions of temperature and pressure used for a particular catalyst system to maximise the yield of linear dimers, and to minimise the competing reactions such as isomerization of the feed olefin can be readily established by one skilled in the art.

The dimerization reaction can be carried out in the gas phase or liquid phase, or mixed gas-liquid phase, depending upon the volatility of the feed olefin and product olefins.

The dimerization reaction may be carried out in the presence of an inert solvent which may also be the carrier for the catalyst system and/or feed olefin. Suitable solvents include alkanes, alkenes, cycloalkanes, and aromatic hydrocarbons. For example, solvents that may be suitably used in the process of the present invention heptane, isooctane, cyclohexane, benzene, toluene, and xylene.

Reaction times of from 0.1 to 10 hours have been found to be suitable, dependent on the activity of the catalyst. The reaction is preferably carried out in the absence of air or moisture.

The dimerization reaction may be carried out in a conventional fashion. It may be carried out in a stirred tank reactor, wherein the feed olefin and catalyst system or catalyst precursors are added continuously to a stirred tank and the feed olefin and catalyst system are removed from the stirred tank with the product olefin, which may then be separated, and optionally the unused feed olefin and/or the catalyst system are recycled back to the stirred tank.

Alternatively, the reaction may be carried out in a batch reactor, wherein the catalyst system or the catalyst system precursors, and feed olefin are charged to an autoclave, and after being reacted for an appropriate time, product is separated from the reaction mixture by conventional means, such as distillation.

The product of dimerization or co-dimerization comprises linear olefin product(s) of 2n or n1+n2 carbon atoms, and unreacted feed linear olefin of n, or n1 and n2, carbon atoms. The product may also comprise by-products such as isomerized feed linear olefin e.g. linear 2-olefin isomer. Thus the product of dimerizing 1-butene comprises linear octenes, unreacted 1-butene and 2-butene.

The product, after separation from catalyst e.g. by distillation, may be used as such in the transmerization step without any other purification at all. It may however be purified first e.g. by distillation to remove at least some of any solvent or diluent from the dimerization. Any such purification may be as well as, instead of, or combined with, purification to remove e.g. by distillation hydrocarbons of lower volatility than the linear olefin of 2n or n1+n2 carbons; examples of such hydrocarbons are unreacted olefin(s) and/or isomerized olefin. The mixture of unreacted linear 1-olefin or 1-olefins and isomerized 1-olefin or 1-olefins from the dimerization is preferably recycled to the dimerization step for reuse, preferably after having been (re-)isomerized over an isomerization catalyst such as Na/K on alumina, especially at a temperature of 50-200° C. such as 100-150° C., especially under superatmospheric pressure such as 0.1-2 MPa preferably 0.5-1.5 M to generate the thermodynamic equilibrium mixture of linear olefins when the content of the 1-olefin in the recycle mixture is less than the equilibrium concentration, and optionally after separation of some of the isomerized olefin, e.g. by means of distillation.

Thus in a preferred process the olefinic compounds in the dimerization reaction product are distilled from the catalyst residue and separated into a more volatile hydrocarbon fraction containing the unreacted feed and isomers, and the linear olefin product(s) of 2n or n1+n2 carbon atoms, which may or may not be further separated from solvent or diluent before passing to the transmerization stage.

Transmerization

The process of the present invention also comprises a transmerization step, which is carried out after the dimerization/co-dimerization step.

Transmerization comprises a combination of step (b)(i) and step (b)(ii) as follows: b(i) reacting the linear internal olefin having 2n carbon atoms produced in dimerization step (a) with a trialkylaluminium compound in the presence of a catalytic amount of an isomerization/displacement catalyst in order to cause isomerization of the linear internal olefin and to displace alkyl groups from said trialkylaluminium compound to form an alkyl aluminium compound wherein at least one of the alkyl groups bound to aluminium is a linear alkyl which has been derived from the isomerization of said linear internal olefin, and (b)(ii) reacting said alkyl aluminium compound with an alpha olefin optionally in the presence of a displacement catalyst so as to displace said linear alkyl from said alkyl aluminium compound to form a linear alpha olefin having 2n carbon atoms.

While not wishing to be bound by theory, it is believed that the reaction in step (b)(i) of the linear internal olefin having 2n carbon atoms with a trialkylaluminium compound in the presence of an isomerization/displacement catalyst causes isomerization of the linear internal olefin to form at least some linear alpha olefin, which linear alpha olefin displaces alkyl groups from said trialkylaluminium compound to form an alkyl aluminium compound wherein at least one of the alkyl groups bound to aluminium is a linear alkyl derived from said linear alpha-olefin.

The linear internal olefin having 2n carbon atoms is preferably reacted with the trialkylaluminium compound, in a molar ratio in the range of from 1:1 to 50:1, preferably from 2:1 to 4:1.

Preferred catalysts for use in step (b)(i) are those catalysts which catalyze both isomerization and displacement, hence the use of the term "isomerization/displacement catalyst". The isomerization/diplacement catalyst for use in step (b)(i) can be any catalyst suitable for isomerizing an internal olefinic double bond, but is preferably a nickel based isomerization/displacement catalyst, such as those disclosed in U.S. Pat. Nos. 5,124,465 and 5,191,145, which are herein incorporated by reference in their entirety. The isomerization/displacement catalyst used herein is preferably selected from nickel (II) salts, nickel (II) carboxylates, nickel (II) acetonates and nickel (O) complexes, which may be stabilized by means of a trivalent phosphorus ligand.

Examples of nickel (II) salts include nickel halides e.g. nickel (II) chloride, nickel (II) bromide, nickel (II) iodide, and their hydrates. Also useful are nickel (II) oxide and nickel (II) hydroxide.

Examples of suitable nickel salts include carboxylates, carbamates, alkoxides, thiolates, catecholates, oxalates, thiocarboxylates, tropolates, phosphinates, acetylacetonates, iminoacetylacetonates, bis-iminoacetylacetonates, the solubility of which can be tuned by an appropriate choice of substituents, as well known to those skilled in the art.

Preferred metal salts for use herein are the optionally substituted acetylacetonates, or x, (x+2)-alkanedionates, where x is an intege e.g. 2 to 6 such as 2,4-alkanedionates and 3,5-alkanedionates. When the acetylacetonates are substituted, preferred substituents are $C_1$-$C_6$ alkyl groups, especially methyl. Examples of suitable acetylacetonates include 2,4-pentanedionates, 2,2,6,6-tetramethyl-3,5-heptanedionates. Other examples are aryl substituted y, (y+2)-alkanedionates such as 1-phenyl-1,3-butanedionates and 1,3-diphenyl-1,3-propanedionates. Preferred acetylacetonates for use herein are the 2,4-pentanedionates.

Examples of nickel (II) carboxylates include nickel acetate, nickel 2-ethylhexanoate, nickel octanoate and nickel naphthenate.

An example of nickel acetonates includes nickel (II) acetylacetonate.

Examples of Ni(0) complex catalysts include $Ni(CO)_4$ and nickel (0) olefin complexes such as nickel bis-1,5-cyclooctadiene $(Ni(COD)_2)$, $Ni(C_2H_4)_3$, $Ni(norbornene)_3$ and nickel cyclododecatriene.

A particularly preferred isomerization/displacement catalyst for use in step (b)(i) is nickel bis-1,5-cyclooctadiene $(Ni(COD)_2)$.

Separate catalysts can be used for the isomerization and the displacement provided that they do not interfere with each other. Examples of displacement catalysts include, for example, colloidal Ni, Pt, Co, nickel acetylacetonate, cobalt carboxylates, e.g. cobalt naphthenate or cobalt acetate, nickel carboxylates, e.g. nickel naphthenate and the like.

The trialkylaluminium compounds suitable for use in the process of the present invention are known to those skilled in the art. Preferably, the alkyl groups of the trialkylaluminium compounds contain fewer carbons than the predominant carbon number of 2n of the internal olefins. Suitable alkyl aluminium compounds which contain alkyl groups having from 2 to 24 or 2-18 carbon atoms, preferably from 2 to 12 carbon atoms, include, for example, triethylaluminium, tri-n-propylaluminium, tri-n-butylaluminium, tri-isobutylaluminium, tri-n-hexylaluminium, tri-n-octylaluminium, tri-n-decylaluminium, tri-n-dodecylaluminium, tri-n-tetradecylaluminium, tri-n-hexadecylaluminium, tri-n-octadecylaluminium, and the like. A particularly preferred trialkyl aluminium compound for use in step (b)(i) is tri-n-propylaluminium.

According to isomerization/displacement step (b)(i), the isomerization/displacement catalyst can be added to a mixture of trialkyl aluminium and internal olefin. Alternatively, the catalyst can be first mixed with the internal olefin(s) and this mixture can be added to the trialkylaluminium. Both isomerization and displacement can be simultaneously carried out in the same vessel. Alternatively, the isomerization reaction can be initiated in a first reactor and then fed to a second reactor containing the trialkylaluminium. The reaction can be carried out in a batch or continuous manner.

In order to favour the replacement of the alkyl groups by the isomerized internal olefins, the displaced alkyl groups in the form of their corresponding 1-olefins can be removed as vapour from the reaction mixture and can be used in the recovery of isomerized 1-olefins by back-displacement. Unreacted internal olefins can be separated from the reaction mixture using conventional methods such as by distillation or vacuum stripping and can be recycled to the isomerization/displacement step (b)(i).

Suitable reaction temperatures for the isomerization/displacement step are in the range of from −20° C. to 200° C., preferably from 30° C. to 100° C. Suitable reaction pressures range from 0-0.689 MPa (0 to 100 psia), preferably 0.0069-0.31 Mpa (1 to 45 psia) and reaction times usually range from 0.1 to 2 hours.

Solvents are not necessary for the isomerization/displacement reaction but can be used if desirable. Suitable solvents include inert aliphatic and aromatic hydrocarbons.

It is sometimes advantageous, especially when using a reactor in which distillation is also taking place, to include an inert diluent such as isoheptane, heptane, octane, or isooctane in the feed.

Thus in a preferred process, the isomerization/displacement stage is performed in the presence of a solvent or diluent at least some of which remains with the organo-aluminium product at the end of the reaction. The reaction can be encouraged to go to completion by distillation of the olefin displaced from the trialkyl aluminium added to step (b)(i) to leave a solution or suspension of the product organo-aluminium product together with catalyst.

This solution or suspension can be used as such in the back displacement step (b)(ii) without purification, or may be treated to separate the catalyst first especially if it is insoluble, before the organo-aluminium product is used in step (b) (ii).

Step (b)(ii) is a displacement reaction wherein the alkyl groups from the isomerized internal olefins are back-displaced from the trialkyl aluminium compounds formed in the isomerization/displacement reaction, by reaction of the trialkyl aluminium compounds with a suitable alpha olefin. The displaced 1-olefin recovered from the isomerization/displacement reaction as described above can be used as the alpha olefin to back-displace the linear 1-olefin from the aluminium alkyl. The regenerated trialkyl aluminium can then be recycled back to the isomerization/displacement reaction. Alternatively, a different olefin can be used for displacement step (b)(ii). Alpha olefins having from 2 to 18 carbon atoms e.g. of 3-7 carbon atoms, and mixtures of such olefins are suitable for use in displacement step (b)(ii); mixtures comprising such an olefin, such as 1-butene, and its internal olefin isomer such as 2-butene, or Raffinate II may be used in step (b)(ii). A particularly preferred alpha olefin for use in displacement step (b)(ii) is propene.

The amount of alpha olefin used in the displacement reaction should be in stoichiometric excess over the amount required to replace all alkyl groups, preferably at least a 200% excess, such as a 200-3000% excess.

The alpha olefin used for displacement in step b(ii) may be fresh olefin or a mixture thereof with displaced 1-olefin from step b(i). The displacing alpha olefin may comprise an equilibrium or non equilibrium mixture of 1-olefin and at least one internal isomer thereof having the same carbon skeleton; examples of such mixtures are mixtures of 1-butene and 2-butene, preferably those produced as a result of isomerization, optionally after removal of some internal olefin such as 2-butene e.g. by distillation. The alpha olefin used for displacement may also comprise excess of olefin unreacted in step b(ii) and recycled. Thus preferably the displacement olefin is a mixture of olefin displaced from step b(i) and olefin unreacted from step b(ii). When the displacing olefin is isomerizable under the reaction conditions of step (b) (ii), the unreacted olefin stream from step b(ii) may also comprise isomerized olefin such as internal olefin, e.g. 2-butene when 1-butene is the displacing olefin. The content of isomer in the unreacted stream can be reduced by back isomerization, over an isomerization catalyst and under conditions such as those described above for isomerizing the mixture of linear 1 olefin and isomerized 1-olefin leaving from the dimerization.

Displacement step (ii) can be carried out in the absence of a catalyst, but is preferably carried out in the presence of a suitable amount of a displacement catalyst. Preferred displacement catalysts are those which do not have any significant isomerization activity under the conditions used. Examples of suitable displacement catalysts include, for example, cobalt carboxylates such as cobalt naphthenate and the like. Nickel complexes such as nickel acetylacetonate, nickel carboxylates such as nickel naphthenate and nickel acetate can be used if combined with lead or other suitable materials to prevent isomerization.

The displacement reaction (b)(ii) is suitably carried out at a reaction temperature of from −10° C. to 200° C., such as 0 to 100° C. and especially 0 to 50° C. Step b(ii) may be performed at a temperature about the same as step b(i) e.g. plus or minus 10° C., but preferably step b(ii) is at a lower temperature such as 30-80° C. lower. If the displacement reaction is carried out in the absence of a catalyst higher temperatures may be required.

The displacement reaction is generally carried out over a period of from 30 seconds to 1 hour (at 25° C.), preferably from 1 minute to 20 minutes.

The back displacement process liberates a linear alpha olefin derived from the linear internal olefin fed to the isomerization/displacement stage (b)(i) and produces a trialkyl aluminium based on the displacing olefin added to stage (b)(ii). The reaction product mixture from step (b)(ii) also usually contains back displacement catalyst and often unreacted back displacement olefin. It may contain some residual catalyst from stage (b)(i). In addition, in particular when using a nickel based displacement catalyst, it may have been desirable to have added a poison such as a lead or copper poison or a cyclic olefin e.g. cyclooctadiene in order to stop stage (b)(ii) when the back displacement is substantially complete and before too much side reaction has taken place. Under these circumstances such a poison has to be separated if the trialkyl aluminium is to be recycled to step (b)(i). The metals may be separated by filtration and the cyclic olefin may be separated by distillation. Thus preferably at the end of step (b)(ii) the product reaction mixture contains the product alpha olefin, unreacted displacement olefin, organoaluminium compound and possibly but preferably solvent/diluent, and/or displacement catalyst and isomerization catalyst, which had been carried over from step (b)(i) and optionally poison. Distillation of the reaction mixture can separate the product olefin and any residual unreacted displacement olefin and optionally at least some of the solvent/diluent from the remainder. After removal from the remainder of any poison and catalysts, e.g. by filtration or distillation the organoaluminium compound can then be recycled to step (b)(i). The used nickel isomerization catalyst from step (b)(i) may have reduced isomerization activity but enough displacement activity for step (b)(ii) so extra displacement catalyst and optionally poison may not necessarily be needed. Thus advantageously the nickel catalyst and an organo aluminium compound may be used in step (b)(i) and then for step (b)(ii) and then back in step b(ii), the nature of the organo aluminium compound present oscillating between the two steps. The steps (b)(i) and (b)(ii) may be performed in the same reactor or two reactors in series. Unreacted displacement olefin from step b(ii) can be recycled for reuse in that step b(ii).

Thus in a preferred process, 1-butene is dimerized over a dimerization catalyst to form a mixture comprising 2-octene and 3-octene, together with more volatile components comprising 1-butene and 2-butene, and catalyst. The volatile components are separated by distillation, passed to an isomerization stage, where the 2-butene is back isomerized at least partly to 1-butene, preferably with an isomerization catalyst such as Na/K on alumina, especially at a temperature of 50-200° C. such as 100-150° C. and under superatmospheric pressure such as 0.11-2 MPa preferably 0.5-1.5 MPa; 1-butene may if desired then be recovered from the isomerate and recycled for reuse in the dimerization stage. The mixture comprising 2+3-octenes is separated from the dimerization catalyst e.g. by distillation and then passed to step b(i) where it is mixed with tripropyl aluminium and an isomerization/displacement catalyst, such as a Ni compound, to produce an organo aluminium which is an octyl or octyl propyl aluminium and to displace propene which is usually distilled off during the reaction. After the reaction unreacted 2+3-octenes can be separated by distillation from the organo aluminium which is then used in step b(ii). At least a molar excess of propene, comprising displaced propene from step b(i) and unreacted recyled propene from step b(ii), is then reacted in step b(ii) with the organo aluminium usually in the presence of displacement catalyst to form tripropylaluminium and liberate 1-octene. The 1-octene can be separated by distillation from the excess of propene and any by products such as hexenes. The residue from the 1-octene separation, may be purified by separation of displacement catalyst, if any, and then recycled to step b(i).

An appropriate transalkylation process carried out under isomerizing conditions for use herein is described in U.S. Pat. Nos. 5,124,465 and 5,191,145, which are herein incorporated by reference in their entirety. The context of these applications is an integral part of the present invention and is incorporated herein by reference.

The overall process of the present invention may also advantageously be performed with recycle of by product or unreacted olefin streams from one of steps (a) and (b) for use as feed olefin streams for the other step. The integrated process may be performed in a batch, semi batch or preferably continuous manner. The integrated process is performed in particular when the linear alpha olefin is the same in step (a) and b (ii), especially when it is propene and most especially when it is 1-butene.

In a first integrated process, step (b) (ii) is performed with a stoichiometric excess of alpha olefin over the amount required to replace all the alkyl group(s) in said alkyl aluminium compound, and step (b)(ii) leaves an olefin stream containing some unreacted alpha olefin, at least part of which is recycled from step (b)(ii) to step (a). This recycle may be as well as recycle to step (a) of at least some of unreacted alpha olefin which has been separated from dimer product and/or dimerization catalyst at the end of step (a). The recycle olefin streams may separately pass into the dimerization step (a), but are advantageously mixed before entering that step, usually with some fresh linear alpha olefin.

When the linear alpha olefin is propylene, the recycling may be performed without any purification, except possibly from oligomers.

When the linear olefin is 1-butene or other isomerizable olefin such as 1-pentene or 1-hexene, the unreacted olefin stream from step b(ii) may contain corresponding internal olefin isomer, such as 2-butene. At least some of the stream may be recycled to step (a) as such or after isomerization of at least some of the 2-butene or other internal olefin isomer e.g. as described before in relation to work up of olefin from steps (a) or (b)(ii); separation of at least some of the isomer e.g. by distillation or otherwise may also be performed before or after the isomerization. The mixture of alpha and internal olefin isomers from step (b)(ii) may be isomerized separately from any isomerization of the linear olefin from step (a) and the products, if desired after separation of internal isomer, passed separately to step (a); advantageously the olefin streams from steps (a) and (b)(ii) are recycled together to the isomerization from whence only one purified olefin stream passes to step (a). The recycled olefin stream passed to step (a) can be an equilibrium or non equilibrium mixture of alpha and internal olefins.

In a second integrated process, step (a) produces linear internal olefin of 2n carbon atoms and leaves one olefin stream comprising unreacted olefin of n carbon atoms, which are separated and at least some of the latter is passed to step b(ii) for use as at least part of the displacing alpha olefin. This recycle may be as well as recycle to step (b)(ii) of by-product/unreacted olefin from step (b)(ii) and also passage of olefin-1 displaced from step (b)(i) to (b)(ii). In the case of 1-butene or other isomerizable alpha olefin, the unreacted olefin stream from step (a) may also comprise 2-butene or other internal isomer and may be purified to reduce its isomer content, in a manner as described above, such as by isomerization and/or separation before passage of at least some of said purified stream to step (b)(ii).

In a third integrated process, some of the by-product/unreacted olefin from step (a) is passed, if desired after purification as described, to step (a) and some to step (b)(ii). In an extension of this type of process, by-product/unreacted olefin from step (b)(ii) meets by product olefin from step (a) before passage, if desired via purification as described, to both step (a) and step (b)(ii).

A fourth aspect of an integrated process can be applied to 1-butene, or other isomerizable alpha olefin, as both feed olefin for step (a) and displacement olefin for step (b)(ii). This process is a modification of the first to third types of integrated process in which the olefin mixture of linear alpha olefin and its isomer from step (a) and/or step (b)(ii) is isomerized with the isomerization/displacement catalyst of step (b)(i), usually in the isomerization part of step (b)(i). The olefin mixture can be isomerized over the isomerization catalyst used in that transmerization in the presence or absence of the trialkylaluminium. The olefin mixture may be passed concurrently with the olefin dimer over the isomerization/displacement catalyst in step (b)(i). Preferably the olefin mixture and olefin dimer are passed alternately over the isomerization/displacement catalyst. The olefin mixture may be passed over a first portion of isomerization/displacement catalyst in a first reactor while the olefin dimer is passed over a second portion of isomerization/displacement catalyst in a second reactor; the first and second reactors may be in parallel. This approach may allow optimization of conditions for each reactor. The operation in parallel also allows continuous isomerization of the olefin mixture in the first reactor while the transmerization is performed semi continuously in the second reactor e.g. with periodic removal of solvent and/or catalyst and/or alkyl aluminium. Conditions of the isomerization over the step (b)(i) catalyst may be as described above for the transmerization step (b)(i) but are preferably under superatmospheric pressure such as 0.11-2 MPa, preferably 0.5-1.5 MPa.

The isomerate produced in the fourth aspect of an integrated process may be recycled, if desired after purification as described, to at least one of steps (a) and (b)(ii).

The invention will now be illustrated by the following non-limiting examples.

EXAMPLES

The example below demonstrates the conversion of 1-butene into linear 1-octene using the process of the present invention.

General Procedures and Characterisation

All chemicals used in preparations were purchased from Aldrich and used without further purification unless mentioned otherwise.

All the operations with the catalyst systems were carried out under nitrogen atmosphere. All solvents used were dried using standard procedures.

Anhydrous o-xylene (>97% purity) was stored over Na-wire and 4 Å molecular sieves (final water content of about 3 ppm).

1-butene (grade 2.0, i.e. 99.0% purity) were purchased from Hoek Loos N.V., Dieren, The Netherlands and was used without further purification.

The products obtained were characterised by Gas Chromatography (GC), in order to evaluate yield of C4, C8 and C12 compounds using a HP 5890 series II apparatus and the following chromatographic conditions:

Column: HP-1 (cross-linked methyl siloxane), film thickness=0.25 μm, internal diameter=0.25 mm, length 60 m (by Hewlett Packard); injection temperature: 325° C.; detection temperature: 325° C.; initial temperature: 40° C. for 10 minutes; temperature programme rate: 10.0° C./minute; final temperature: 325° C. for 41.5 minutes; internal standard: o-xylene or hexadecane.

The NMR data was obtained at room-temperature with a Varian 300 MHz or 400 MHz apparatus.

Transition Metal Complex and Catalyst Preparation

The transition metal catalyst composition used in the dimerization experiments below was a solution in xylene of 2-[1-(2-t-butylphenylimino)ethyl]-6-[1-(4-eicosanoxy-3,5-diphenylphenylimino)ethyl]pyridine cobalt[II] chloride (B) and sodium tetrakis[3,5-bis(trifluoromethyl)phenyl]borate (a cationic catalyst solution). The preparation of this catalyst composition, including various starting materials, is described below.

Preparation of 4-hydroxy-3,5-diphenylacetanilide

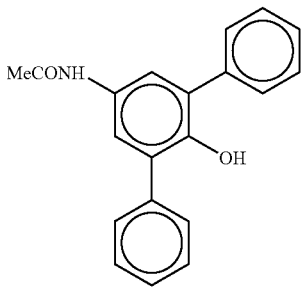

To 4-hydroxy-3,5-diphenylaniline (4 g, 15.3 mmol) in 30 ml of ethanol was added 1.6 ml of acetic anhydride. The reaction was stirred for 16 hours. The resulting mixture was poured into water. The pink product (6 g) was isolated by filtration, washed with water, dried and used without further purification.

$^1$H-NMR (CDCl$_3$, selected data) δ 5.31(s, OH), 2.16 (s, Me).

Preparation of 4-eicosanoxy-3,5-diphenylacetanilide

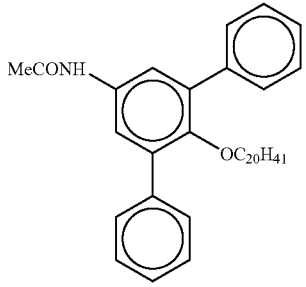

A mixture of 4-hydroxy-3,5-diphenylacetanilide (6 g), 1-bromoeicosane and 10 g potassium carbonate was refluxed in acetone (70 ml) for 16 hours. The reaction mixture was poured into water. The product was isolated by filtration, washed with water and dried. Crystallisation from pentane yielded 7.2 g of 4-eicosanoxy-3,5-diphenylacetanilide as a white solid.

$^1$H-NMR (CDCl$_3$, selected data) δ 3.13(t, CH$_2$O), 2.17 (s, Me).

Preparation of 4-eicosanoxy-3,5-diphenylaniline

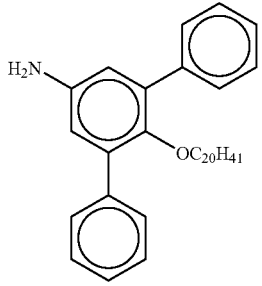

To 4-eicosanoxy-3,5-diphenylacetanilide (7.2 g) was added 24 g NaOH in 30 ml H$_2$O and 40 ml ethanol. The resulting mixture was refluxed for 16 hours. The reaction mixture was poured on ice. The product was isolated by filtration and washed with water. Crystallisation from ethanol yielded 5.9 g (10.9 mmol) of 4-eicosanoxy-3,5-diphenylaniline as a white solid.

$^1$H-NMR (CDCl$_3$) δ 7.27-7.63 (m, 10H, ArH), 6.67 (s, 2H, ArH), 3.60 (br s, 2H, NH$_2$), 3.09 (t, 2H, CH$_2$O), 0.8-1.4 (m, 39H, alkyl).

Preparation of 2-[1-(2-t-butylphenylimino)ethyl]-6-[1-(4-eicosanoxy-3,5-diphenylphenylimino)ethyl] pyridine (A)

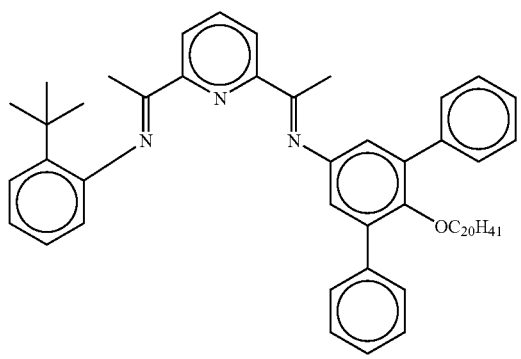

2-[1-(2-t-butylphenylimino)ethyl]-6-acetylpyridine (487 mg, 1.65 mmol), prepared according to the method described in US 2005/0059786, and 4-eicosanoxy-3,5-diphenylaniline (900 mg, 1.65 mmol) were dissolved in 50 ml of toluene. To this solution, 4 Å molecular sieves were added. After standing for 1 day the mixture was filtered. The solvent was removed in vacuo. The residue was crystallised from ethanol. The product A was isolated as an yellow solid (600 mg, 0.73 mmol, 44%).

$^1$H-NMR (CDCl$_3$) δ 8.38 (dd, 2H, Py-H$_m$), 7.90 (t, 1H, Py-H$_p$), 6.5-7.7 (m, 16H, ArH), 3.21 (t, 2H, CH$_2$O), 2.52 (s, 3H, Me), 2.40 (s, 3H, Me), 1.37 (s, 9H, t-Bu), 0.8-1.35(m, 39H, alkyl).

Preparation of 2-[1-(2-t-butylphenylimino)ethyl]-6-[1-(4-eicosanoxy-3,5-diphenylphenylimino)ethyl] pyridine cobalt[II] chloride complex, (B)

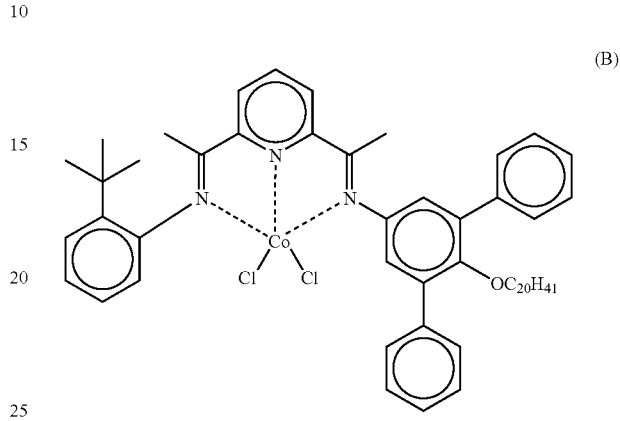

In an inert atmosphere a solution of 300 mg (0.365 mmol) diimine A in 10 ml dichloromethane was added to 40 mg CoCl$_2$ (0.308 mmol) in 5 ml dichloromethane. The mixture was stirred for 16 hours. After filtration the solution was concentrated by removing part of the solvent in vacuo. The product formed a jelly after addition of 10 ml pentane to the resulting solution (~2 ml). A yellowish brown solid was isolated by centrifugation, washing with pentane and drying in vacuo. Yield 234 mg (80%) of the cobalt complex B.

$^1$H-NMR(C$_6$D$_6$, broad signals, selected data) δ 113 (1H, Py-H$_m$), 112 (1H, Py-H$_m$), 18 (1H, Py-H$_p$), −10.8 (9H, t-Bu), −56.0 (2H, ArH), −85.6 (1H, ArH).

Preparation of a Cationic Catalyst Solution In Situ

In an inert atmosphere sodium tetrakis[3,5-bis(trifluoromethyl)phenyl]borate (ABCR GmbH & Co, Karlsruhe, Germany) was added to a solution of an equimolar amount of cobalt complex B in o-xylene. The solution was stirred for half an hour at room temperature prior to injection in the autoclave. The amount of cobalt complex B used is given below.

Alpha-Olefin Dimerizations in a 0.5-Liter Batch Autoclave

The dimerization experiments were performed in a 0.5 liter steel autoclave equipped with jacket cooling with a heating/cooling bath (ex. Julabo, model no. ATS-2) and a turbine/gas stirrer and baffles. In order to avoid traces of water, the reactor was kept under nitrogen pressure (0.5 MPa) at room temperature. Prior to the experiment the reactor was scavenged by introducing 250 ml o-xylene, MMAO (0.3 g solution in heptane) and subsequent stirring at 70° C. under nitrogen pressure of 0.5-0.6 MPa for 30 min. The reactor contents were discharged via a tap in the base of the autoclave. The reactor was evacuated to 0.4 kPa and cooled to 20° C., after which it was loaded with 120 ml 1-butene (grade 2.0, Hoek Loos) and the reactor was heated to 30° C.

Under stirring, the MMAO-solution (1207 micromoles) was then added to the reactor with the aid of o-xylene (the MMAO-solution was injected, the injector was subsequently rinsed twice) and the stirring at 800 rpm was continued for 60 minutes.

The required amount (49 μmol) of the cationic catalyst solution, preparation of which is described above, was introduced into the stirred reactor using an injection system, after which the injector was rinsed three times with o-xylene. The total amount of o-xylene introduced in the reactor was 13 ml.

The addition of the catalyst system resulted in a small exotherm (generally 3-8° C.), which was easily absorbed by the thermostat bath, bringing the reactor back to the initial conditions.

After about 3 hours, an aliquot of the reaction mixture was taken for analyses and the reaction was allowed to continue for another 17 hours. After 20 hours and 40 minutes the experiment was stopped by depressurising the autoclave and decanting under inert atmosphere the product mixture into a collection bottle using a tap in the base of the autoclave.

The amount and purity of C4, C8 and C12 olefins in the reaction mixture was determined by gas chromatography after quenching the sample with diluted sulphuric acid and using the introduced o-xylene as internal standard. According to this method, 27.6 g of a mixture of cis and trans 2-octene and 3-octene and 0.4 g of $C_{12}$ s were made. The ratio of the internal 2- and 3-octenes over all octenes formed in the reaction was 98.4%. On the basis of the GC data the turnover number to $C_8$ s was 10,000 mol 1-butene/mol of Co. The percentage of 2-butene over 1-butene+2-butene in the $C_4$ fraction was found to be 34.2%.

Analysis of the sample taken after 3 hours reaction time showed the formation of 9.8 g of internal octenes with selectivity of 98.4%, similar to the 20.5 hours sample. Turnover number was 3,550 mol 1-butene/mol of Co. The percentage of 2-butene over 1-butene+2-butene in the $C_4$ fraction was found to be 8.6%.

The collected reaction mixture was transferred under inert conditions to a distillation device and, still under inert conditions the butenes present were slowly evaporated off at room temperature. Subsequently, the remaining fraction was distilled at room temperature under vacuum, the volatiles collected in two fractions at low temperatures (−78° C.), and stored under inert conditions. Gas chromatography of the first fraction (5 ml) showed it to be mainly heptane. Gas chromatography of the second fraction showed it to consist of the $C_8$ fraction, o-xylene, and a small amount of heptane (solvent of MMAO). The $C_8$ content of the second fraction was 75 w % with the same percentage internal olefins as the original sample. This product was used in the transmerization experiment described hereafter.

In a pressure vessel 4.0 g of olefin mixture described above (26.8 mmol) were weighed in under inert conditions together with 64 mg n-hexadecane (internal standard), 0.5 g of Al(n-$C_6H_{13}$)$_3$ (94.9% purity) and 215 mg of Ni(COD)$_2$ dissolved in heptane (3 mg of Ni(COD)$_2$/g of heptane amounting to 30 ppm Ni on total intake). The reaction vessel was heated for 2 hours at 80° C., subsequently cooled to room temperature and the volatiles of the obtained reaction mixture were distilled off at this temperature under vacuum. After distillation 0.67 g of residue remained while 4.07 g volatiles were collected as distillate. GC analysis of the distillate did not show the presence of any n-hexadecane. A sample of 90 mg of the residue was diluted in pentane, quenched with diluted sulphuric acid, and the organic products analyzed by gas chromatography. GC showed the presence of a $C_6$ fraction consisting of n-hexane, of a $C_8$ fraction consisting of n-octane, and some $C_{12}$ impurities. On the basis of the $C_6$ and $C_8$ data the formula of the original Al compound can be calculated as Al($C_6H_{13}$)$_{0.76}$($C_8H_{17}$)$_{2.24}$.

The residue obtained from the experiment described above, 0.58 g, was reacted with 8.06 g (95.9 mmol) of 1-hexene in the presence of 88 mg Co naphthenate in nonane (1.2 mg of Co/g of nonane amounting to 10 ppm Co on total intake). After stirring the reaction mixture 15 minutes at room temperature, a sample was taken, quenched with acid, and the organic components analyzed by means of gas chromatography. GC showed the presence of a $C_8$ fraction consisting of 93.1% 1-octene, 4.5% (n-octane+octene isomer), 2.2% internal octenes, and 0.2% unidentified products. From the 4.5% (n-octane+octene isomer) fraction at the most 0.6% is attributable to the octene isomer. The total selectivity to linear octenes defined as the selectivity to 1-octene+selectivity to n-octane is 97.0%.

GC analyses of a sample taken after 30 minutes of reaction showed the same results.

This example shows that 1-butene can be converted to linear 1-octene using the process of the present invention with high yield and high selectivity.

Instead of the trihexylaluminium, an equivalent amount of tri n-butylaluminium may be used in step (b)(i) and a 10-fold molar excess of 1-butene in the back displacement step (b)(ii) to liberate 1-octene in high yield and selectivity.

The excess of 1-butene from step (b)(ii), which may contain a little 2-butene can be recycled for reuse in step (b)(ii) and/or recycled for reuse in the dimerization, optionally after isomerization to an equilibrium mixture of 1-butene and 2-butene, by heating at 120° C. in the presence of a Na/K on alumina catalyst under pressure.

Propene Conversion

This Example demonstrates the conversion of 1-propene to 1-hexene using the process of the present invention.

The dimerization experiment was performed in a 0.5 liter steel autoclave equipped with jacket cooling with a heating/cooling bath (ex. Julabo, model no. ATS-2) and a turbine/gas stirrer and baffles. In order to avoid traces of water, the reactor was kept under nitrogen pressure (0.5 MPa) at room temperature. Prior to the experiment the reactor was scavenged by introducing 250 ml toluene, MAO (0.3 g solution in toluene) and subsequent stirring at 70° C. under nitrogen pressure of 0.5-0.6 MPa for 30 min. The reactor contents were discharged via a tap in the base of the autoclave. The reactor was evacuated to 0.4 kPa and cooled to 20° C., after which it was loaded with 51 g propene (grade 2.5, Hoek Loos N.V.) and 160 ml toluene. The reactor was subsequently heated to 50° C. giving a pressure of 8.4 barg.

Under stirring, the MAO-solution (4 mmol) was then added to the reactor with the aid of toluene (the MAO-solution was injected, the injector was subsequently rinsed twice) and the stirring at 800 rpm was continued for 30 minutes.

The required amount (40 μmol) of the cationic catalyst solution, preparation of which is described above with the only difference that toluene was used as the solvent instead of o-xylene, was introduced into the stirred reactor using an injection system, after which the injector was rinsed three times with toluene. The total amount of toluene introduced in the reactor was 200 ml.

The addition of the catalyst system resulted in a small exotherm (generally 2-7° C.), which was easily absorbed by the thermostat bath, bringing the reactor back to the initial conditions.

After 14 minutes a weighed amount of hexylbenzene (1 g) was injected into the reactor to serve as internal standard for GC analysis. Directly afterwards (after 16 minutes) the experiment was stopped by depressurising the autoclave and decanting under inert atmosphere the product mixture into a collection bottle, containing diluted sulphuric acid (to deactivate the catalyst), using a tap in the base of the autoclave.

The amount and purity of C6, C9 and C12 olefins in the reaction mixture were determined by gas chromatography using the introduced hexylbenzene as internal standard. According to this method, 9.8 g of $C_6$ s, 1.0 g of $C_9$ s and 0.07 g of $C_{12}$ s were made. In the $C_6$ fraction the ratio of 1-hexene to cis/trans 2-hexene was 39:60. The ratio of the linear hexenes over all hexenes formed in the reaction was 98.9%. On the basis of the GC data the turnover number to propene oligomers was 11,600 mol propene/mol of Co. The conversion of propene was found to be 21.4%.

After removal of propene, the solvent, hexylbenzene and the higher oligomers of propene by vacuum distillation under inert conditions the 1+2-hexene mixture may be used in a transmerization experiment to be carried out analogous to the above-described transmerization experiment with internal octenes, but now using trioctylaluminium instead of trihexylaluminium in the transmerization step (b)(i) and using 1-octene instead of 1-hexene in the final back displacement step (b)(ii).

The transmerization step (b)(i) may be performed as generally described according to the procedure of Ex 14A of U.S. Pat. No. 5,124,465 with an equivalent amount of trioctylaluminium instead of tripropylaluminium. The back displacement step (b)(ii) may be performed as generally described according to the procedure of Ex 14 B of EP 505834A with 1-octene. A high yield and selectivity of formation of 1-hexene may be obtained.

Instead of the trioctylaluminium, an equivalent amount of tri-n-propylaluminium may be used in step (b)(i) and, instead of 1-octene a 10 fold molar excess of propylene may be used in the back displacement step (b)(ii). The excess of propylene from step (b)(ii) can be recycled for reuse in step (b)(ii) and/or recycled for reuse in the dimerization.

The invention claimed is:

1. A process for the preparation of linear alpha olefins having 2n carbon atoms from linear alpha olefins having n carbon atoms comprising the steps of:
    (a) dimerizing a linear alpha olefin having n carbon atoms in the presence of a dimerization catalyst comprising (i) one or more transition metal complexes each comprising a transition metal atom and a bis-arylimine pyridine ligand and (ii) a co-catalyst compound to produce a linear internal olefin having 2n carbon atoms;
    (b)(i) reacting the linear internal olefin having 2n carbon atoms produced in step (a) with a trialkylaluminium compound in the presence of a catalytic amount of an isomerization/displacement catalyst in order to cause isomerization of the linear internal olefin and to displace alkyl group(s) from said trialkylaluminium compound to form an alkyl aluminium compound wherein at least one of the alkyl groups bound to aluminium is a linear alkyl which has been derived from the isomerization of said linear internal olefin, and
    (b)(ii) reacting said alkyl aluminium compound with an alpha olefin optionally in the presence of a displacement catalyst so as to displace said linear alkyl from said alkyl aluminium compound to form a linear alpha olefin having 2n carbon atoms.

2. The process of claim 1 wherein n is an integer in the range of from 3 to 11.

3. The process of claim 1 wherein the starting alpha olefin having n carbon atoms comprises 1-butene and the linear alpha olefin having 2n carbon atoms comprises 1-octene.

4. The process of claim 1 wherein said trialkyl aluminium compound is selected from the group consisting of tri-n-hexylaluminium, tri-isobutylaluminium, tri-n-butylaluminium, triethylaluminium, tri-n-propylaluminium, tri-n-octylaluminium, tri-n-decylaluminium, tri-n-dodecylaluminium, tri-n-tetradecylaluminium, tri-n-hexadecylaluminium, tri-n-octadecylaluminium, and mixtures thereof.

5. The process of claim 1 wherein the isomerization catalyst is a nickel catalyst selected from the group consisting of nickel (II) salts, nickel (II) carboxylates, nickel (II) acetonates and nickel (0) complexes, and mixtures thereof.

6. The process of claim 1 wherein the bis-arylimine pyridine ligand has the formula (I) below:

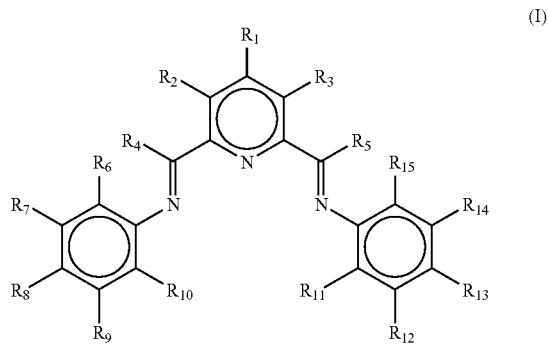

(I)

wherein $R_1$-$R_5$, $R_7$-$R_9$, $R_{12}$ and $R_{14}$ are each, independently, hydrogen, optionally substituted hydrocarbyl, an inert functional group, or any two of $R_1$-$R_3$ and $R_7$-$R_9$ vicinal to one another taken together may form a ring, and $R_6$ is hydrogen, optionally substituted hydrocarbyl, an inert functional group, or taken together with $R_7$ or $R_4$ to form a ring, $R_{10}$ is hydrogen, optionally substituted hydrocarbyl, an inert functional group, or taken together with $R_9$ or $R_4$ to form a ring, $R_{11}$ is hydrogen, optionally substituted hydrocarbyl, an inert functional group, or taken together with $R_{12}$ or $R_5$ to form a ring, $R_{15}$ is hydrogen, optionally substituted hydrocarbyl, an inert functional group, or taken together with $R_{14}$ or $R_5$ to form a ring, provided that $R_{13}$ and at least one of $R_{12}$ and $R_{14}$ are independently selected from optionally substituted $C_1$-$C_{30}$ alkyl, optionally substituted $C_4$-$C_{30}$ alkyloxy, halogen and optionally substituted $C_5$-$C_{20}$ aryl, or $R_{13}$ taken together with $R_{12}$ or $R_{14}$ form a ring, or $R_{12}$ taken together with $R_{11}$ form a ring and $R_{14}$ taken together with $R_{15}$ form a ring, and provided that at least one of $R_{12}$, $R_{13}$ and $R_{14}$ is optionally substituted $C_4$-$C_{30}$ alkyloxy.

7. The process of claim 1 wherein the transition metal atom is selected from Fe and Co.

8. The process of claim 1 wherein the co-catalyst compound is selected from the group consisting of alkyl aluminiums, aluminoxanes and mixtures thereof.

9. The process of claim 1 wherein the linear alpha olefin in step (a) is the same as the alpha olefin in step (b)(ii).

10. The process of claim 9 wherein step (b)(ii) is performed with a stoichiometric excess of alpha olefin over the amount required to replace all the alkyl group(s) in said alkyl aluminium compound, and step (b)(ii) leaves an olefin stream containing some unreacted alpha olefin, at least part of which is reycled from step (b)(ii) to step (a).

11. The process of claim 10 wherein the alpha olefin is 1-butene said olefin stream comprises 2-butene, and at least some of the 2-butene in the stream is isomerized to 1-butene before use in step (a).

12. The process of claim 9 wherein step (a) produces the linear internal olefin of 2n carbons and leaves an olefin stream comprising unreacted olefin of n carbon atoms, at least some of said olefin stream being passed to step (b)(ii) as at least part of the alpha olefin reacting with the alkyl aluminium compound.

13. The process of claim 12 wherein the alpha olefin is 1-butene, said olefin stream comprises 2-butene, and at least some of the 2-butene in said stream is isomerized to 1-butene before passage of at least some to step (b)(ii).

14. The process of of claim 11 wherein the isomerization is performed with the isomerization/displacement catalyst of step (b)(i).

15. A process for the preparation of a linear alpha olefin having (n1+n2) carbon atoms comprising the steps of:
  (a) co-dimerizing a linear alpha olefin having n1 carbon atoms with a linear alpha olefin having n2 carbon atoms in the presence of a dimerization catalyst comprising (i) one or more transition metal complexes each comprising a transition metal atom and a bis-arylimine pyridine ligand and (ii) a co-catalyst compound to produce a linear internal olefin having (n1+n2) carbon atoms;
  (b)(i) reacting the linear internal olefin having (n1+n2) carbon atoms produced in step (a) with a trialkylaluminium compound in the presence of a catalytic amount of an isomerization/displacement catalyst in order to cause isomerization of the linear internal olefin and to displace alkyl group(s) from said trialkylaluminium compound to form an alkyl aluminium compound wherein at least one of the alkyl groups bound to aluminium is a linear alkyl which has been derived from the isomerization of said linear internal olefin having (n1+n2) carbon atoms, and
  (b)(ii) reacting said alkyl aluminium compound with an alpha olefin optionally in the presence of a displacement catalyst so as to displace said linear alkyl from said alkyl aluminium compound to form a linear alpha olefin having (n1+n2) carbon atoms.

16. The process of claim 15 wherein n1 and n2 are each integers in the range of from 3 to 11 and wherein n1 is a different integer from n2.

17. The process of claim 15 wherein said trialkyl aluminium compound is selected from the group consisting of tri-n-hexylaluminium, tri-isobutylaluminium, tri-n-butylaluminium, triethylaluminium, tri-n-propylaluminium, tri-n-octylaluminium, tri-n-decylaluminium, tri-n-dodecylaluminium, tri-n-tetradecylaluminium, tri-n-hexadecylaluminium, tri-n-octadecylaluminium, and mixtures thereof.

18. The process of claim 15 wherein the isomerization catalyst is a nickel catalyst selected from the group consisting of nickel (II) salts, nickel (II) carboxylates, nickel (II) acetonates and nickel (O) complexes, and mixtures thereof.

19. The process of claim 15 wherein the bis-arylimine pyridine ligand has the formula (I) below:

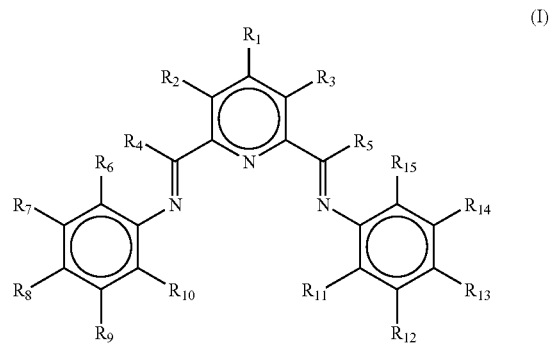

(I)

wherein $R_1$-$R_5$, $R_7$-$R_9$, $R_{12}$ and $R_{14}$ are each, independently, hydrogen, optionally substituted hydrocarbyl, an inert functional group, or any two of $R_1$-$R_3$ and $R_7$-$R_9$ vicinal to one another taken together may form a ring, and $R_6$ is hydrogen, optionally substituted hydrocarbyl, an inert functional group, or taken together with $R_7$ or $R_4$ to form a ring, $R_{10}$ is hydrogen, optionally substituted hydrocarbyl, an inert functional group, or taken together with $R_9$ or $R_4$ to form a ring, $R_{11}$ is hydrogen, optionally substituted hydrocarbyl, an inert functional group, or taken together with $R_{12}$ or $R_5$ to form a ring, $R_{15}$ is hydrogen, optionally substituted hydrocarbyl, an inert functional group, or taken together with $R_{14}$ or $R_5$ to form a ring, provided that $R_{13}$ and at least one of $R_{12}$ and $R_{14}$ are independently selected from optionally substituted $C_1$-$C_{30}$ alkyl, optionally substituted $C_4$-$C_{30}$ alkyloxy, halogen and optionally substituted $C_5$-$C_{20}$ aryl, or $R_{13}$ taken together with $R_{12}$ or $R_{14}$ form a ring, or $R_{12}$ taken together with $R_{11}$ form a ring and $R_{14}$ taken together with $R_{15}$ form a ring, and provided that at least one of $R_{12}$, $R_{13}$ and $R_{14}$ is optionally substituted $C_4$-$C_{30}$ alkyloxy.

* * * * *